United States Patent
Hammer et al.

(10) Patent No.: US 10,449,333 B2
(45) Date of Patent: Oct. 22, 2019

(54) GUIDEWIRE FEEDER

(71) Applicant: VALTECH CARDIO, LTD., Or Yehuda (IL)

(72) Inventors: Tal Hammer, Ramat Gan (IL); Meir Kutzik, Ramat Gan (IL); Tal Reich, Moledet (IL); Alexei Koifman, Bat Yam (IL)

(73) Assignee: Valtech Cardio, Ltd., Or Yehuda (IL)

( * ) Notice: Subject to any disclaimer, the term of this patent is extended or adjusted under 35 U.S.C. 154(b) by 1128 days.

(21) Appl. No.: 14/209,171

(22) Filed: Mar. 13, 2014

(65) Prior Publication Data

US 2014/0276648 A1    Sep. 18, 2014

Related U.S. Application Data

(60) Provisional application No. 61/782,121, filed on Mar. 14, 2013.

(51) Int. Cl.
*A61B 5/00*     (2006.01)
*A61M 25/09*    (2006.01)

(52) U.S. Cl.
CPC .......... *A61M 25/09041* (2013.01); *A61M 2025/09116* (2013.01)

(58) Field of Classification Search
CPC ........... A61M 25/09; A61M 25/09041; A61M 25/0105; A61M 2025/09125; A61M 25/0113; A61M 25/0662; A61B 2017/22038; A61B 2017/22047
USPC .......................................... 600/585; 606/108
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |
| 3,840,018 A | 10/1974 | Heifetz |
| 3,898,701 A | 8/1975 | La Russa |

(Continued)

FOREIGN PATENT DOCUMENTS

| | | |
|---|---|---|
| EP | 0611561 | 8/1994 |
| EP | 06/14342 | 9/1994 |

(Continued)

OTHER PUBLICATIONS

An English Translation of an Office Action dated Nov. 24, 2015, which issued during the prosecution of Israel Patent Application No. 223448. (the relevant part only).

(Continued)

*Primary Examiner* — May A Abouelela
(74) *Attorney, Agent, or Firm* — Thomas C. Richardson

(57) ABSTRACT

Apparatus for use with a guidewire is provided, the apparatus including (1) a first housing, shaped to define a first channel through which the guidewire is slidable; (2) a second housing, shaped to define a second channel through which the guidewire is slidable in at least a first direction toward the first housing; (3) a guidewire-engaging element, disposed within the second housing, and configured to inhibit the guidewire from sliding through the second channel in a second direction away from the first housing; and (4) a tubular member, (a) shaped to define a lumen therethrough, through which the guidewire is slidable, and (b) coupled to the second housing and slidably coupled to the first housing. Other embodiments are also described.

20 Claims, 9 Drawing Sheets

(56) References Cited

U.S. PATENT DOCUMENTS

| | | |
|---|---|---|
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A * | 9/1994 | Greelis ............ A61M 25/0119 604/271 |
| 5,450,860 A | 9/1995 | O'Connor |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | William et al. |
| 5,716,370 A | 2/1998 | Williamson, IV et al. |
| 5,716,397 A | 2/1998 | Myers |
| 5,730,150 A * | 3/1998 | Peppel ............ A61M 25/09041 600/585 |
| 5,749,371 A * | 5/1998 | Zadini ............ A61M 25/09041 600/481 |
| 5,810,882 A | 9/1998 | Bolduc et al. |
| 5,824,066 A | 10/1998 | Gross |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern et al. |
| 6,110,200 A | 8/2000 | Hinnenkamp |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,315,784 B1 | 11/2001 | Djurovic |
| 6,319,281 B1 | 11/2001 | Patel |
| 6,332,893 B1 | 12/2001 | Mortier et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,862 B2 | 7/2006 | Vidlund et al. |
| 7,087,064 B1 | 8/2006 | Hyde |
| 7,101,395 B2 | 9/2006 | Tremulis et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |

(56) References Cited

U.S. PATENT DOCUMENTS

| | | |
|---|---|---|
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,238,191 B2 | 7/2007 | Bachmann |
| 7,288,097 B2 | 10/2007 | Seguin |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,753,924 B2 | 7/2010 | Starksen et al. |
| 7,871,368 B2 | 1/2011 | Zollinger et al. |
| 7,871,433 B2 | 1/2011 | Lattouf |
| 7,927,370 B2 | 4/2011 | Webler et al. |
| 7,927,371 B2 | 4/2011 | Navia et al. |
| 7,942,927 B2 | 5/2011 | Kaye et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,800 B2 | 2/2012 | McCarthy et al. |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,226,711 B2 | 7/2012 | Mortier et al. |
| 8,231,671 B2 | 7/2012 | Kim |
| 8,241,351 B2 | 8/2012 | Cabiri |
| 8,252,050 B2 | 8/2012 | Maisano et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,430,926 B2 | 4/2013 | Kirson |
| 8,460,370 B2 | 6/2013 | Zakay et al. |
| 8,460,371 B2 | 6/2013 | Hlavka et al. |
| 8,475,491 B2 | 7/2013 | Milo |
| 8,500,800 B2 | 8/2013 | Maisano et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,591,576 B2 | 11/2013 | Hasenkam et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,715,342 B2 | 5/2014 | Zipory et al. |
| 8,728,097 B1 | 5/2014 | Sugimoto et al. |
| 8,734,467 B2 | 5/2014 | Miller et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,790,367 B2 | 7/2014 | Nguyen et al. |
| 8,795,298 B2 | 8/2014 | Hernlund et al. |
| 8,845,717 B2 | 9/2014 | Khairkhahan et al. |
| 8,845,723 B2 | 9/2014 | Spence et al. |
| 8,852,272 B2 | 10/2014 | Gross et al. |
| 8,858,623 B2 | 10/2014 | Miller et al. |
| 8,864,822 B2 | 10/2014 | Spence et al. |
| 8,888,843 B2 | 11/2014 | Khairkhahan et al. |
| 8,911,461 B2 | 12/2014 | Traynor et al. |
| 8,911,494 B2 | 12/2014 | Hammer et al. |
| 8,932,348 B2 | 1/2015 | Solem et al. |
| 8,940,042 B2 | 1/2015 | Miller et al. |
| 8,945,211 B2 | 2/2015 | Sugimoto et al. |
| 8,951,285 B2 | 2/2015 | Sugimoto et al. |
| 8,951,286 B2 | 2/2015 | Sugimoto et al. |
| 9,011,520 B2 | 4/2015 | Miller et al. |
| 9,017,399 B2 | 4/2015 | Gross et al. |
| 9,119,719 B2 | 9/2015 | Zipory et al. |
| 9,125,632 B2 | 9/2015 | Loulmet et al. |
| 9,173,646 B2 | 11/2015 | Fabro |
| 9,180,005 B1 | 11/2015 | Lashinski et al. |
| 9,226,825 B2 | 1/2016 | Starksen et al. |
| 9,427,316 B2 | 8/2016 | Schweich, Jr. et al. |
| 2001/0021874 A1 | 9/2001 | Carpentier et al. |
| 2001/0044656 A1 | 11/2001 | Williamson, IV et al. |
| 2002/0029080 A1 | 3/2002 | Mortier et al. |
| 2002/0042621 A1 | 4/2002 | Liddicoat et al. |
| 2002/0082525 A1* | 6/2002 | Oslund ............ A61M 25/0169 600/585 |

(56) References Cited

U.S. PATENT DOCUMENTS

| | | |
|---|---|---|
| 2002/0087048 A1 | 7/2002 | Brock et al. |
| 2002/0103532 A1 | 8/2002 | Langberg et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177904 A1 | 11/2002 | Huxel et al. |
| 2002/0188301 A1 | 12/2002 | Dallara et al. |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0130731 A1 | 7/2003 | Vidlund et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0122448 A1 | 6/2004 | Levine |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133274 A1 | 7/2004 | Webler et al. |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0236419 A1 | 11/2004 | Milo |
| 2004/0243227 A1 | 12/2004 | Starksen et al. |
| 2004/0249453 A1 | 12/2004 | Cartledge et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010787 A1 | 1/2005 | Tarbouriech |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187613 A1 | 8/2005 | Bolduc et al. |
| 2005/0192596 A1 | 9/2005 | Jugenheimer et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0256532 A1 | 11/2005 | Nayak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0052868 A1 | 3/2006 | Mortier et al. |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0112359 A1 | 2/2007 | Kimura et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0083168 A1 | 4/2007 | Whiting et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0233239 A1 | 10/2007 | Navia et al. |
| 2007/0239208 A1 | 10/2007 | Crawford |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |

(56) References Cited

U.S. PATENT DOCUMENTS

| | | |
|---|---|---|
| 2007/0255400 A1 | 11/2007 | Parravicini et al. |
| 2007/0270755 A1* | 11/2007 | Von Oepen ..... A61M 25/09041 604/164.13 |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1* | 3/2008 | Marchand ............ A61F 2/2433 604/103.02 |
| 2008/0065204 A1 | 3/2008 | Macoviak et al. |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0125861 A1 | 5/2008 | Webler et al. |
| 2008/0140116 A1 | 6/2008 | Bonutti |
| 2008/0167714 A1 | 7/2008 | St. Goar et al. |
| 2008/0177382 A1 | 7/2008 | Hyde et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228265 A1* | 9/2008 | Spence ............ A61B 17/00234 623/2.36 |
| 2008/0243245 A1 | 10/2008 | Thambar et al. |
| 2008/0262609 A1 | 10/2008 | Gross et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0300629 A1 | 12/2008 | Surti |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0149872 A1 | 6/2009 | Gross et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1 | 7/2009 | Milo |
| 2009/0222083 A1* | 9/2009 | Nguyen ............ A61B 17/00234 623/2.11 |
| 2009/0248148 A1 | 10/2009 | Shaolian et al. |
| 2009/0259307 A1 | 10/2009 | Gross et al. |
| 2009/0264994 A1 | 10/2009 | Saadat |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023117 A1 | 1/2010 | Yoganathan et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049313 A1 | 2/2010 | Alon et al. |
| 2010/0063542 A1 | 3/2010 | van der Burg et al. |
| 2010/0063586 A1 | 3/2010 | Hasenkam et al. |
| 2010/0076499 A1 | 3/2010 | McNamara et al. |
| 2010/0094248 A1 | 4/2010 | Nguyen et al. |
| 2010/0121349 A1 | 5/2010 | Meier et al. |
| 2010/0130992 A1 | 5/2010 | Machold et al. |
| 2010/0152845 A1 | 6/2010 | Bloom et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0198347 A1 | 8/2010 | Zakay et al. |
| 2010/0211166 A1 | 8/2010 | Miller et al. |
| 2010/0217382 A1 | 8/2010 | Chau et al. |
| 2010/0234935 A1 | 9/2010 | Bashiri et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0324598 A1 | 12/2010 | Anderson |
| 2011/0004298 A1 | 1/2011 | Lee et al. |
| 2011/0011917 A1 | 1/2011 | Loulmet |
| 2011/0029066 A1 | 2/2011 | Gilad et al. |
| 2011/0066231 A1 | 3/2011 | Cartledge et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0166649 A1 | 7/2011 | Gross et al. |
| 2011/0184510 A1 | 7/2011 | Maisano et al. |
| 2011/0190879 A1 | 8/2011 | Bobo et al. |
| 2011/0202130 A1 | 8/2011 | Cartledge et al. |
| 2011/0208283 A1 | 8/2011 | Rust |
| 2011/0224785 A1 | 9/2011 | Hacohen |
| 2011/0230961 A1 | 9/2011 | Langer et al. |
| 2011/0238088 A1 | 9/2011 | Bolduc et al. |
| 2011/0257633 A1 | 10/2011 | Cartledge et al. |
| 2011/0257728 A1 | 10/2011 | Kuehn |
| 2011/0264208 A1 | 10/2011 | Duffy et al. |
| 2011/0276062 A1 | 11/2011 | Bolduc |
| 2011/0282361 A1 | 11/2011 | Miller et al. |
| 2011/0288635 A1 | 11/2011 | Miller |
| 2011/0301698 A1 | 12/2011 | Miller et al. |
| 2012/0022557 A1 | 1/2012 | Cabiri et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035712 A1 | 2/2012 | Maisano et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0123531 A1 | 5/2012 | Tsukashima et al. |
| 2012/0136436 A1 | 5/2012 | Cabiri et al. |
| 2012/0143323 A1 | 6/2012 | Hasenkam et al. |
| 2012/0150290 A1 | 6/2012 | Gabbay |
| 2012/0158021 A1 | 6/2012 | Morrill |
| 2012/0191182 A1 | 7/2012 | Hauser et al. |
| 2012/0197388 A1 | 8/2012 | Khairkhahan et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1* | 10/2012 | Whittaker ......... A61M 25/0158 600/585 |
| 2012/0283757 A1 | 11/2012 | Miller et al. |
| 2012/0296417 A1 | 11/2012 | Hill et al. |
| 2012/0296419 A1 | 11/2012 | Richardson et al. |
| 2012/0310330 A1 | 12/2012 | Buchbinder et al. |
| 2012/0323313 A1 | 12/2012 | Seguin |
| 2012/0330410 A1 | 12/2012 | Hammer et al. |
| 2012/0330411 A1 | 12/2012 | Gross et al. |
| 2013/0023758 A1 | 1/2013 | Fabro |

(56) References Cited

U.S. PATENT DOCUMENTS

| | | |
|---|---|---|
| 2013/0035759 A1 | 2/2013 | Gross et al. |
| 2013/0079873 A1 | 3/2013 | Migliazza et al. |
| 2013/0090724 A1 | 4/2013 | Subramanian et al. |
| 2013/0096672 A1 | 4/2013 | Reich et al. |
| 2013/0096673 A1 | 4/2013 | Hill et al. |
| 2013/0116776 A1 | 5/2013 | Gross et al. |
| 2013/0116780 A1 | 5/2013 | Miller et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0172992 A1 | 7/2013 | Gross et al. |
| 2013/0190863 A1 | 7/2013 | Call et al. |
| 2013/0190866 A1 | 7/2013 | Zipory et al. |
| 2013/0197632 A1 | 8/2013 | Kovach et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakay et al. |
| 2013/0289718 A1 | 10/2013 | Tsukashima et al. |
| 2013/0304093 A1 | 11/2013 | Serina et al. |
| 2014/0018914 A1 | 1/2014 | Zipory et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0222137 A1 | 8/2014 | Miller et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0257475 A1 | 9/2014 | Gross et al. |
| 2014/0275757 A1 | 9/2014 | Goodwin et al. |
| 2014/0276648 A1 | 9/2014 | Hammer et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0343668 A1 | 11/2014 | Zipory et al. |
| 2014/0379006 A1 | 12/2014 | Sutherland et al. |
| 2015/0012087 A1 | 1/2015 | Miller et al. |
| 2015/0018940 A1 | 1/2015 | Quill et al. |
| 2015/0051697 A1 | 2/2015 | Spence et al. |
| 2015/0127097 A1 | 5/2015 | Neumann et al. |
| 2015/0272734 A1 | 10/2015 | Sheps et al. |
| 2015/0351906 A1 | 12/2015 | Hammer et al. |

FOREIGN PATENT DOCUMENTS

| | | |
|---|---|---|
| EP | 10/06905 | 6/2000 |
| EP | 0954257 | 8/2000 |
| EP | 1258437 A1 | 11/2002 |
| EP | 0871417 | 10/2003 |
| EP | 1266641 | 10/2004 |
| EP | 1034753 | 2/2005 |
| EP | 1562522 | 12/2008 |
| EP | 1258232 | 1/2009 |
| EP | 1420723 | 1/2009 |
| EP | 1903991 | 9/2009 |
| EP | 1418865 | 10/2009 |
| EP | 1531762 | 4/2010 |
| EP | 2273928 | 1/2011 |
| EP | 1450733 | 2/2011 |
| EP | 2445417 | 5/2012 |
| EP | 11792047.0 | 10/2012 |
| EP | 1861045 | 3/2015 |
| EP | 1465555 | 5/2015 |
| IL | 223448 | 12/2012 |
| WO | 1992/005093 | 4/1992 |
| WO | 1993/010714 | 6/1993 |
| WO | 1996/039963 | 12/1996 |
| WO | 1996/040344 | 12/1996 |
| WO | 1997/001369 | 1/1997 |
| WO | 1998/046149 | 10/1998 |
| WO | 1999/030647 | 6/1999 |
| WO | 2000/009048 | 2/2000 |
| WO | 2000/022981 | 4/2000 |
| WO | 2001/026586 | 4/2001 |
| WO | 2001056457 | 8/2001 |
| WO | 2002/085250 | 10/2002 |
| WO | 2002/085251 | 10/2002 |
| WO | 2002/085252 | 10/2002 |
| WO | 03/028558 | 4/2003 |
| WO | 2003/047467 | 6/2003 |
| WO | 2003/049647 | 6/2003 |
| WO | 03/105667 | 12/2003 |
| WO | 2004/103434 | 12/2004 |
| WO | 2005/021063 | 3/2005 |
| WO | 2005/046488 | 5/2005 |
| WO | 2005/062931 | 7/2005 |
| WO | 2006/012013 | 2/2006 |
| WO | 2006/012038 | 2/2006 |
| WO | 2006/086434 | 8/2006 |
| WO | 2006/097931 | 9/2006 |
| WO | 2006/105084 | 10/2006 |
| WO | 2006/116558 | 11/2006 |
| WO | 2007/011799 | 1/2007 |
| WO | 2007/136783 | 11/2007 |
| WO | 2008/014144 | 1/2008 |
| WO | 2008/031103 | 3/2008 |
| WO | 2008/068756 | 6/2008 |
| WO | 2009/130631 | 10/2009 |
| WO | 2010/004546 | 1/2010 |
| WO | 2010/006905 | 1/2010 |
| WO | 10/044851 A1 | 4/2010 |
| WO | 2010/065274 | 6/2010 |
| WO | 2010/073246 | 7/2010 |
| WO | 2010/085649 | 7/2010 |
| WO | 2010/128502 | 11/2010 |
| WO | 2010/128503 | 11/2010 |
| WO | 2010/150178 | 12/2010 |
| WO | 2011/051942 | 5/2011 |
| WO | 2011/067770 | 6/2011 |
| WO | 2011/089601 | 7/2011 |
| WO | 2011/111047 | 9/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/068541 | 5/2012 |
| WO | 2012/176195 | 12/2012 |
| WO | 2013/021374 | 2/2013 |
| WO | 2013/021375 | 2/2013 |
| WO | 2013/069019 | 5/2013 |
| WO | 2013/088327 | 6/2013 |
| WO | 2014/064694 | 5/2014 |
| WO | 2014/064695 | 5/2014 |
| WO | 2014/076696 | 5/2014 |
| WO | 2014/087402 | 6/2014 |
| WO | 2014/115149 | 7/2014 |
| WO | 2014/195786 | 12/2014 |
| WO | 2016/087934 | 6/2016 |

OTHER PUBLICATIONS

An Office Action dated Oct. 5, 2015, which issued during the prosecution of U.S. Appl. No. 14/246,417.

An Office Action dated Oct. 1, 2015, which issued during the prosecution of U.S. Appl. No. 14/141,228.

European Search Report dated Sep. 25, 2015 which issued during the prosecution of Applicant's European App No. 09794095.1.

(56) References Cited

OTHER PUBLICATIONS

European Search Report dated Nov. 4, 2015 which issued during the prosecution of Applicant's European App No. 10772091.4.
European Search Report dated Nov. 16, 2015 which issued during the prosecution of Applicant's European App No. 10826224.7.
An Office Action dated Jan. 4, 2016, which issued during the prosecution of U.S. Appl. No. 14/589,100.
An Office Action dated Jan. 6, 2016, which issued during the prosecution of U.S. Appl. No. 14/128,756.
An International Search Report and a Written Opinion both dated Jan. 25, 2016, which issued during the prosecution of Applicant's PCT/IL2015/051027.
An Office Action dated Jan. 5, 2016, which issued during the prosecution of U.S. Appl. No. 14/084,426.
An Office Action dated Jan. 5, 2016, which issued during the prosecution of U.S. Appl. No. 14/027,934.
An Office Action dated Jul. 30, 2015, which issued during the prosecution of U.S. Appl. No. 13/319,007.
An Office Action dated Aug. 7, 2015, which issued during the prosecution of U.S. Appl. No. 14/128,756.
An English translation of an Office Action dated Jul. 17, 2015 which issued during the prosecution of Chinese Patent Application No. 201080059948.4.
An Office Action dated Jun. 18, 2015, which issued during the prosecution of U.S. Appl. No. 14/551,951.
An Office Action dated Jun. 18, 2015, which issued during the prosecution of U.S. Appl. No. 13/319,030.
An Office Action dated Jun. 11, 2015, which issued during the prosecution of European Patent Application No. 11811934.6.
An International Search Report and a Written Opinion both dated May 12, 2015, which issued during the prosecution of Applicant's PCT/IL2014/050914.
European Search Report dated Apr. 29, 2015, which issued during the prosecution of Applicant's European App No. 14200202.
A Chinese Office Action dated Dec. 12, 2013 in CN Application No. 200980157331.3.
A Notice of Allowance dated Apr. 3, 2013, which issued during the prosecution of U.S. Appl. No. 12/563,930.
A Notice of Allowance dated Apr. 27, 2012, which issued during the prosecution of U.S. Appl. No. 12/341,960.
A Notice of Allowance dated Jan. 7, 2014, which issued during the prosecution of U.S. Appl. No. 12/926,673.
A Notice of Allowance dated Jun. 26, 2012, which issued during the prosecution of U.S. Appl. No. 12/608,316.
A Notice of Allowance dated May 2, 2013, which issued during the prosecution of U.S. Appl. No. 12/843,412.
A Notice of Allowance dated May 22, 2013, which issued during the prosecution of U.S. Appl. No. 12/689,635.
A Notice of Allowance dated May 24, 2012, which issued during the prosecution of U.S. Appl. No. 12/563,952.
A Notice of Allowance dated Sep. 18, 2012, which issued during the prosecution of U.S. Appl. No. 12/706,868.
A Restriction Requirement dated Apr. 1, 2011, which issued during the prosecution of U.S. Appl. No. 12/608,316.
A Restriction Requirement dated Apr. 19, 2010, which issued during the prosecution of U.S. Appl. No. 12/341,960.
A Restriction Requirement dated Feb. 4, 2013, which issued during the prosecution of U.S. Appl. No. 13/141,606.
A Restriction Requirement dated Jan. 6, 2012, which issued during the prosecution of U.S. Appl. No. 12/795,026.
A Restriction Requirement dated Jul. 5, 2012, which issued during the prosecution of U.S. Appl. No. 12/563,930.
A Restriction Requirement dated Jul. 12, 2011, which issued during the prosecution of U.S. Appl. No. 12/437,103.
A Restriction Requirement dated Mar. 30, 2012, which issued during the prosecution of U.S. Appl. No. 12/785,717.
A Restriction Requirement dated May 1, 2012, which issued during the prosecution of U.S. Appl. No. 12/843,412.
A Restriction Requirement dated Nov. 19, 2012, which issued during the prosecution of U.S. Appl. No. 12/926,673.
A Restriction Requirement dated Nov. 2, 2012, which issued during the prosecution of U.S. Appl. No. 13/167,492.
A Restriction Requirement dated Nov. 14, 2011 which issued during the prosecution of U.S. Appl. No. 12/548,991.
A Restriction Requirement dated Oct. 25, 2012 which issued during the prosecution of U.S. Appl. No. 13/167,444.
A Restriction Requirement dated Sep. 14, 2012, which issued during the prosecution of U.S. Appl. No. 12/795,192.
Communication dated Feb. 1, 2011, which issued during the prosecution of Applicant's European Patent Application No. EP 07849540.
A Supplementary European Search Report dated Dec. 4, 2012, which issued during the prosecution of European Patent Application No. EP 09834225.6.
Agarwal et al International Cardiology Perspective Functional Tricuspid Regurgitation, Circ Cardiovasc Interv 2009;2;2;565-573 (2009).
Alfieri et al "Novel Suture Device for Beating-Heart Mitral Leaflet Approximation", Ann Thorac Surg 2002, 74:1488-1493.
Alfieri et al, "An effective technique to correct anterior mitrel leaflet prolapse," J Card Surg 14(6):468-470 (1999).
A Supplementary European Search Report dated Mar. 28, 2013, which issued during the prosecution of European Patent Application No. EP 10772091.4.
Alfieri et al, "The double orifice technique in mitrel valve repair: a simple solution for complex problems," Journal of Thoracic Cardiovascular Surgery 122:674-681 (2001).
Alfieri et al, "The edge to edge technique," The European Association for Cardia-Thoracic Surgery 14th Annual Meeting Oct. 7-11, Book of Process (2000).
Alfieri, "The edge-to-edge repair of the mitral valve," Abstract 6th Annual New Era Cardiac Care: Innovation & Technology, Heart Surgery Forum pp. 103 (2003).
Amplatzer Cardiac Plug brochure (English pages), AGA Medical Corporation (Plymouth, MN) (copyright 2008-2010, downloaded Jan. 11, 2011).
Amplatzer Cribriform Occluder A Patient's Guide to Percutaneous, Transcatheter, Atrial Septal Defect Closure AGA Medical Corporation, Apr. 2008.
Amplatzer Septal Occluder A patient guide to the Non-Surgical Closure of the Atrial Septal Defect Using the Amplatzer Septal Occluder System, AGA Medical Corporation, 0412008.
An Advisory Action dated Sep. 6, 2012 which issued during the prosecution of U.S. Appl. No. 12/548,991.
An English translation of an Office Action dated Apr. 23, 2014 which issued during the prosecution of Chinese Patent Application No. 201080059948.4.
An English translation of an office Action dated Jul. 25, 2014 which issued during the prosecution of Chinese Patent Application No. 200980157331.3.
An International Preliminary Report on Patentability dated Nov. 9, 2011, which issued during the prosecution of Applicant's PCT/IL2010/000357.
An International Preliminary Report on Patentability dated Dec. 18, 2010, which issued during the prosecution of Applicant's PCT/IL09/00593.
An International Preliminary Report on Patentability dated Dec. 23, 2014, which issued during the prosecution of Applicant's PCT/IL2012/050451.
U.S. Appl. No. 61/733,979, filed Dec. 6, 2012.
U.S. Appl. No. 61/820,979, filed May 8, 2013.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL20 1 1/000600.
An International Preliminary Report on Patentability dated Jun. 29, 2011, which issued during the prosecution of Applicant's PCT/IL2009/001209.
An International Preliminary Report on Patentability dated Jun. 5, 2012, which issued during the prosecution of Applicant's PCT/IL2010/001024.

(56) References Cited

OTHER PUBLICATIONS

An International Preliminary Report on Patentability dated May 1, 2012, which issued during the prosecution of Applicant's PCT/IL2010/000890.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Search Report and a Written opinion both dated Aug. 17, 2010, which issued during the prosecution of Applicant's PCT/IL10/00357.
An International Search Report and a Written opinion both dated Feb. 22, 2013, which issued during the prosecution of Applicant's PCT/IL2012/50451.
An International Search Report and a Written opinion both dated Feb. 10, 2011, which issued during the prosecution of Applicant's PCT/IL2010/000890.
An International Search Report and a Written opinion both dated Dec. 6, 2012, which issued during the prosecution of Applicant's PCT/IL2012/000250.
An International Search Report and a Written opinion both dated Nov. 8, 2010, which issued during the prosecution of Applicant's PCT/IL2010/000358.
An International Search Report and a Written Opinion both dated Nov. 14, 2011, which issued during the prosecution of Applicant's PCT/IL2011/000404.
An International Search Report and a Written opinion both dated Nov. 23, 2011, which issued during the prosecution of Applicant's PCT/IL2011/000446.
An International Search Report and a Written opinion both dated Apr. 9, 2014, which issued during the prosecution of Applicant's PCT/IL2013/050860.
An International Search Report dated Feb. 2, 2012, which issued during the prosecution of Applicant's PCT/IL2011/000600.
An International Search Report dated Jun. 10, 2010, which issued during the prosecution of Applicant's PCT/IL09/01209.
An International Search Report dated May 19, 2011, which issued during the prosecution of Applicant's PCT/IL2011/00064.
An International Search Report dated Sep. 8, 2009, which issued during the prosecution of Applicant's PCT/IL09/00593.
An International Search Report together with Written opinion both dated Mar. 30, 2011, which issued during the prosecution of Applicant's PCT/IL2010/001024.
An Interview Summary dated Jul. 27, 2011, which issued during the prosecution of U.S. Appl. No. 12/341,960.
An Notice of Allowance dated Dec. 7, 2011, which issued during the prosecution of U.S. Appl. No. 12/435,291.
An office Action dated Apr. 2, 2013, which issued during the prosecution of U.S. Appl. No. 12/785,717.
An office Action dated Aug. 13, 2012, which issued during the prosecution of U.S. Appl. No. 13/044,694.
An office Action dated Aug. 24, 2012, which issued during the prosecution of U.S. Appl. No. 12/563,930.
An office Action dated Dec. 31, 2012, which issued during the prosecution of U.S. Appl. No. 13/044,694.
An office Action dated Feb. 14, 2013, which issued during the prosecution of U.S. Appl. No. 13/167,492.
An office Action dated Jan. 17, 2013, which issued during the prosecution of U.S. Appl. No. 13/167,444.
An office Action dated Jul. 18, 2013, which issued during the prosecution of U.S. Appl. No. 13/044,694.
An office Action dated Jul. 20, 2012, which issued during the prosecution of U.S. Appl. No. 12/843,412.
An office Action dated Apr. 1, 2013, which issued during the prosecution of Patent Application No. 13/167,476.
An office Action dated Feb. 12, 2013, which issued during the prosecution of U.S. Appl. No. 12/926,673.
An office Action dated Feb. 3, 2014 which issued during the prosecution of U.S. Appl. No. 12/689,693.
An office Action dated Jun. 11, 2014, which issued during the prosecution of U.S. Appl. No. 14/027,934.
An office Action dated Jun. 4, 2014, which issued during the prosecution of U.S. Appl. No. 12/840,463.
An office Action dated Jun. 7, 2013, which issued during the prosecution of U.S. Appl. No. 13/141,606.
An office Action dated Mar. 9, 2012, which issued during the prosecution of U.S. Appl. No. 12/689,635.
An office Action dated Mar. 27, 2013, which issued during the prosecution of U.S. Appl. No. 12/843,412.
An office Action dated Mar. 29, 2011, which issued during the prosecution of U.S. Appl. No. 12/341,960.
An office Action dated May 6, 2013, which issued during the prosecution of U.S. Appl. No. 12/689,693.
An office Action dated May 10, 2012, which issued during the prosecution of U.S. Appl. No. 12/795,026.
An office Action dated Apr. 6, 2010, which issued during the prosecution of Applicant's U.S. Appl. No. 12/484,512.
An office Action dated Aug. 4, 2010, which issued during the prosecution of U.S. Appl. No. 12/341,960.
An office Action dated Aug. 15, 2013, which issued during the prosecution of U.S. Appl. No. 12/795,192.
An office Action dated Aug. 2, 2011 which issued during the prosecution of U.S. Appl. No. 12/435,291.
An office Action dated Aug. 23, 2013, which issued during the prosecution of U.S. Appl. No. 13/167,444.
An office Action dated Aug. 5, 2010 which issued during the prosecution of U.S. Appl. No. 11/950,930.
An Office Action dated Aug. 6, 2012, which issued during the prosecution of U.S. Appl. No. 12/548,991.
An office Action dated Dec. 18, 2013, which issued during the prosecution of U.S. Appl. No. 13/666,141.
An office Action dated Dec. 29, 2011, which issued during the prosecution of U.S. Appl. No. 12/563,952.
An office Action dated Jan. 23, 2012, which issued during the prosecution of U.S. Appl. No. 12/692,061.
An office Action dated Jan. 27, 2012, which issued during the prosecution of U.S. Appl. No. 12/548,991.
An office Action dated Feb. 17, 2010 which issued during the prosecution of U.S. Appl. No. 11/950,930.
An office Action dated Jan. 17, 2013, which issued during the prosecution of U.S. Appl. No. 12/795,192.
An office Action dated Jul. 6, 2012, which issued during the prosecution of U.S. Appl. No. 12/692,061.
An office Action dated Jun. 10, 2014, which issued during the prosecution of U.S. Appl. No. 13/167,492.
An office Action dated Jun. 13, 2012, which issued during the prosecution of U.S. Appl. No. 12/437,103.
An office Action dated May 5, 2011, which issued during the prosecution of U.S. Appl. No. 12/706,868.
An office Action dated May 19, 2011, which issued during the prosecution of U.S. Appl. No. 12/706,868.
An office Action dated May 30, 2012, which issued during the prosecution of U.S. Appl. No. 12/706,868.
An office Action dated Nov. 5, 2012, which issued during the prosecution of U.S. Appl. No. 12/795,026.
An office Action dated Nov. 14, 2011, which issued during the prosecution of U.S. Appl. No. 12/608,316.
An Office Action dated Nov. 21, 2013, which issued during the prosecution of U.S. Appl. No. 13/167,476.
An office Action dated Nov. 30, 2012, which issued during the prosecution of U.S. Appl. No. 12/689,635.
An office Action dated Oct. 3, 2014, which issued during the prosecution of U.S. Appl. No. 13/749,153.
An office Action dated Oct. 22, 2013, which issued during the prosecution of U.S. Appl. No. 12/926,673.
An office Action dated Oct. 27, 2011, which issued during the prosecution of U.S. Appl. No. 12/563,952.
An office Action dated Jun. 2, 2014, which issued during the prosecution of U.S. Appl. No. 13/319,030.

(56) References Cited

OTHER PUBLICATIONS

An office Action dated Oct. 2, 2013, which issued during the prosecution of U.S. Appl. No. 13/167,492.
An office Action dated Sep. 28, 2011, which issued during the prosecution of U.S. Appl. No. 12/437,103.
An office Action dated Oct. 6, 2010, which issued during the prosecution of Applicant's U.S. Appl. No. 12/484,512.
An office Action dated Oct. 9, 2013, which issued during the prosecution of U.S. Appl. No. 12/996,954.
An office Action dated Sep. 1, 2011, which issued during the prosecution of U.S. Appl. No. 12/706,868.
An office Action dated Sep. 16, 2009 which issued during the prosecution of U.S. Appl. No. 11/950,930.
Communication dated Aug. 22, 2014 from the United States Patent and Trademark Office in counterpart U.S. Appl. No. 14/027,934.
Communication dated Aug. 26, 2014 from the United States Patent and Trademark Office in counterpart U.S. Appl. No. 13/167,444.
Dang NC et al "Simplified Placement of Multiple Artificial Mitral Valve Chords," The Heart Surgery Forum #2005-1005 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Langer et al Ring plus String: Papillary muscle repositioning as an adjunctive repair technique for ischemic mitral regurgitation, The Journal of Thoracic Cardiovascular surgery vol. 133 No. 1, Jan. 2007.
Notice of Allowance dated Jun. 11, 2014, which issued during the prosecution of U.S. Appl. No. 12/689,693.
Notice of Allowance dated Jun. 23, 2014, which issued during the prosecution of U.S. Appl. No. 12/548,991.
Notice of Allowance dated Jun. 25, 2014, which issued during the prosecution of U.S. Appl. No. 13/666,262.
Notice of Allowance dated Mar. 6, 2014, which issued during the prosecution of U.S. Appl. No. 12/437,103.
Notice of Allowance dated Nov. 19, 2013, which issued during the prosecution of U.S. Appl. No. 12/795,192.
Communication dated Oct. 14, 2014 from the United States Patent and Trademark Office in counterpart application No. 13/319,030.
An office Action dated Sep. 29, 2014, which issued during the prosecution of U.S. Appl. No. 13/504,870.
Communication regarding amended claims filed dated Dec. 27, 2012, regarding European Application No. 11792047.0.
Langer et al RING+STRING, Successful Repair technique for ischemic mitral regurgitation with severe leaflet Tethering, The Department of Thoracic Cardiovascular surgery, Hamburg, Germany, Nov. 2008.
Maisano, The double-orifice technique as a standardized approach to treat mitral . . . , European Journal of Cardio-thoracic Surgery 17 (2000) 201-205.
Odell JA et al., "Early Results of a Simplified Method of Mitral Valve Annuloplasty," Circulation 92:150-154 (1995).
Office Action dated Dec. 16, 2013 in U.S. Appl. No. 13/666,262.
Supplementary European Search Report dated Oct. 23, 2014 which issued during the prosecution of Applicant's European App No. 10826224.7.
Supplementary European Search Report dated Jan. 21, 2014 which issued during the prosecution of Applicant's European App No. 11 78 6226.
Swain CP et al., "An endoscopically deliverable tissue-transfixing device for securing biosensors in the gastrointestinal tract," Gastrointestinal Endoscopy 40(6): 730-734 (1994).
Two dimensional real-time ultrasonic imaging of the heart and great vessels, Mayo Clin Proc vol. 53:271-303, 1978.
U.S. Appl. No. 60/902,146, filed Feb. 16, 2007.
U.S. Appl. No. 61/001,013, filed Oct. 29, 2007.
U.S. Appl. No. 61/745,848, filed Dec. 6, 2012.
U.S. Final Office Action dated Dec. 27, 2013, issued in corresponding U.S. Appl. No. 12/785,717.

O'Reilly S et al., "Heart valve surgery pushes the envelope," Medtech Insight 8(3): 73, 99-108 (2006).
Restriction Requirement dated Nov. 14, 2011, which issued during the prosecution of U.S. Appl. No. 12/689,635.
Office Action dated Dec. 19, 2013 in U.S. Appl. No. 14/027,934.
Search Report in European Patent Application 107720906 dated Jan. 17, 2014.
U.S. Appl. No. 60/873,075, filed Dec. 5, 2006.
U.S. Appl. No. 61/132,295, filed Jun. 16, 2008.
U.S. Appl. No. 61/265,936, filed Dec. 2, 2009.
U.S. Appl. No. 61/283,445, filed Dec. 2, 2009.
U.S. Appl. No. 61/555,570, filed Nov. 4, 2011.
U.S. Appl. No. 61/207,908, filed Feb. 17, 2009.
U.S. Appl. No. 61/557,082, filed Nov. 8, 2011.
U.S. Appl. No. 61/717,303, filed Oct. 23, 2012.
An office Action dated Apr. 2, 2015, which issued during the prosecution of U.S. Appl. No. 14/027,934.
An International Search Report and a Written opinion both dated Mar. 21, 2014, which issued during the prosecution of Applicant's PCT/IL2013/050992.
Notice of Allowance dated Feb. 2, 2015, which issued during the prosecution of U.S. Appl. No. 13/504,870.
Notice of Allowance dated Dec. 24, 2014, which issued during the prosecution of U.S. Appl. No. 12/795,026.
Notice of Allowance dated Mar. 24, 2015, which issued during the prosecution of U.S. Appl. No. 14/486,226.
An Office Action dated Mar. 16, 2015, which issued during the prosecution of U.S. Appl. No. 14/084,426.
Notice of Allowance dated Nov. 13, 2014, which issued during the prosecution of U.S. Appl. No. 12/795,026.
Supplementary European Search Report dated Jan. 20, 2015 which issued during the prosecution of Applicant's European App No. 12803037.
Communication dated Jan. 13, 2015, issued by the European Patent Office in corresponding application No. 10834311.2.
Supplementary European Search Report dated Mar. 23, 2015 which issued during the prosecution of Applicant's European App No. 11792047.
Notice of Allowance dated Dec. 20, 2013, which issued during the prosecution of U.S. Appl. No. 12/437,103.
An Office Action dated Jan. 13, 2015, which issued during the prosecution of U.S. Appl. No. 13/707,013.
An Office Action dated Mar. 23, 2015, which issued during the prosecution of U.S. Appl. No. 13/707,013.
U.S. Appl. No. 61/782,121, filed Mar. 14, 2013.
Swenson, O. and Malinin, T.I., 1978: "An improved mechanical device for control of urinary incontinence," Investigative urology, 15(5), pp. 389-391.
Swenson, O.: "An experimental implantable urinary sphincter," Invest Urol. Sep. 1976;14(2):100-3.
European Search Report dated Jun. 24, 2016, which issued during the prosecution of European Patent Application No. EP 12847363.
European Search Report dated Jul. 8, 2016, which issued during the prosecution of Applicant's European App No. 13849843.1.
European Search Report dated Jul. 15, 2016, which issued during the prosecution of Applicant's European App No. 13849947.0.
An Office Action dated Jul. 20, 2016, which issued during the prosecution of U.S. Appl. No. 14/246,417.
Daebritz, S., et al. "Experience with an adjustable pulmonary artery banding device in two cases: initial success-midterm failure." The Thoracic and cardiovascular surgeon 47.01 (1999): 51-52.
Elliott, Daniel S., Gerald W. Timm, and David M. Barrett. "An implantable mechanical urinary sphincter: a new nonhydraulic design concept." Urology52.6 (1998): 1151-1154.
Park, Sang C., et al. "A percutaneously adjustable device for banding of the pulmonary trunk." International journal of cardiology 9.4 (1985): 477-484.
Swenson, Orvar. "Internal device for control of urinary incontinence." Journal of pediatric surgery 7.5 (1972): 542-545.
An Invitation to pay additional fees dated Aug. 18, 2016, which issued during the prosecution of Applicant's PCT/IL2016/050433.
Ahmadi, A., G. Spillner, and Th Johannesson. "Hemodynamic changes following experimental production and correction of acute

(56) References Cited

OTHER PUBLICATIONS mitral regurgitation with an adjustable ring prosthesis." The Thoracic and cardiovascular surgeon36.06 (1988): 313-319.

Ahmadi, Ali, et al. "Percutaneously adjustable pulmonary artery band." The Annals of thoracic surgery 60 (1995): S520-S522.

Assad, Renato S. "Adjustable Pulmonary Artery Banding." (2014).

An English Translation of an Office Action dated Sep. 15, 2016, which issued during the prosecution of Israel Patent Application No. 243837. (the relevant part only).

Non Final Office Action dated Oct. 21, 2016, issued by the U.S. Patent and Trademark Office in U.S. Appl. No. 14/567,472.

ISR & Written Opinion dated Oct. 17, 2016, issued in International Application No. PCT/IL2016/050433.

An Office Action dated May 4, 2016, which issued during the prosecution of U.S. Appl. No. 14/589,100.

An Office Action dated Jun. 17, 2016, which issued during the prosecution of U.S. Appl. No. 14/357,040.

An Office Action dated Jun. 14, 2016, which issued during the prosecution of U.S. Appl. No. 14/273,155.

An Office Action dated Apr. 7, 2016, which issued during the prosecution of U.S. Appl. No. 14/242,151.

Notice of Allowance dated May 3, 2016, which issued during the prosecution of U.S. Appl. No. 13/319,030.

An Office Action dated Apr. 8, 2016, which issued during the prosecution of U.S. Appl. No. 14/141,228.

Notice of Allowance dated Apr. 12, 2016, which issued during the prosecution of U.S. Appl. No. 14/667,090.

An Office Action dated May 11, 2016, which issued during the prosecution of U.S. Appl. No. 14/128,756.

Notice of Allowance dated May 6, 2016, which issued during the prosecution of U.S. Appl. No. 14/667,090.

* cited by examiner

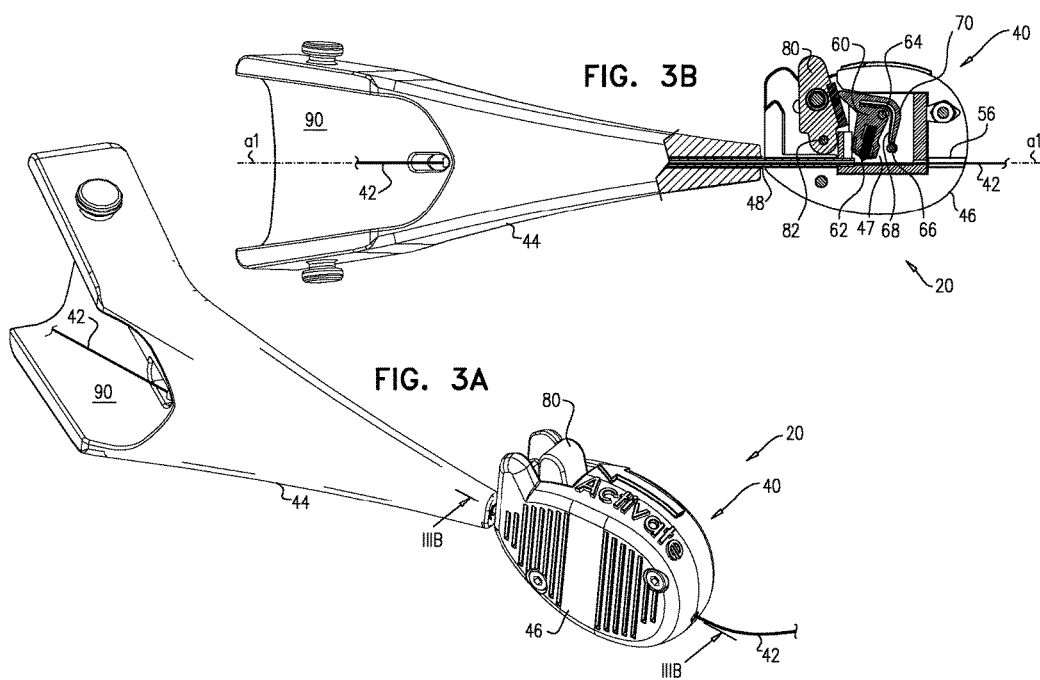

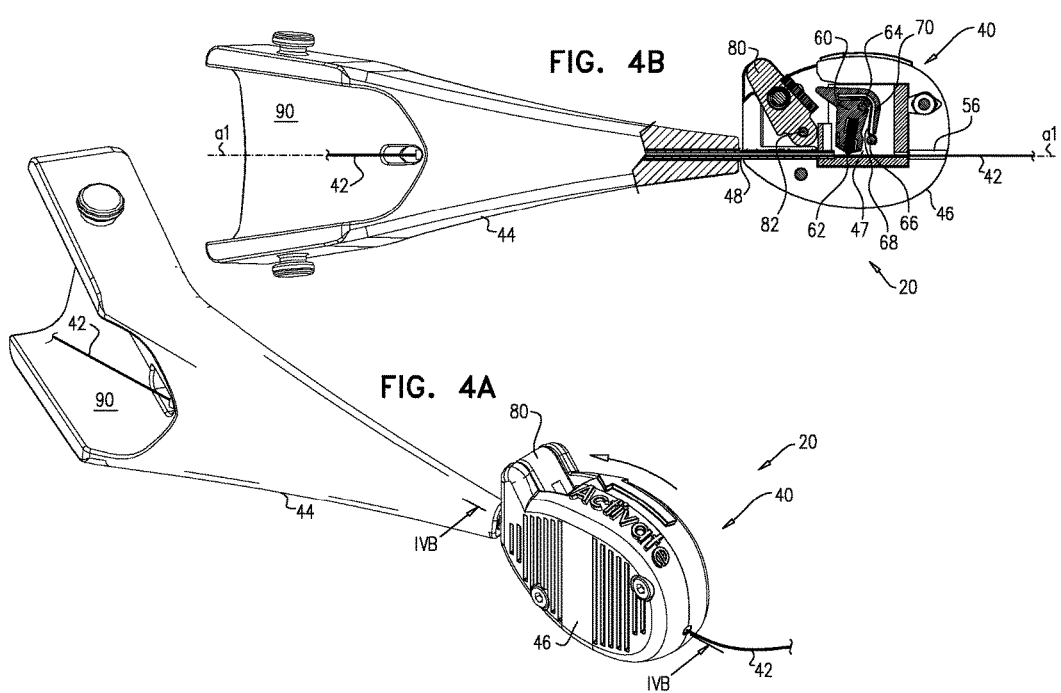

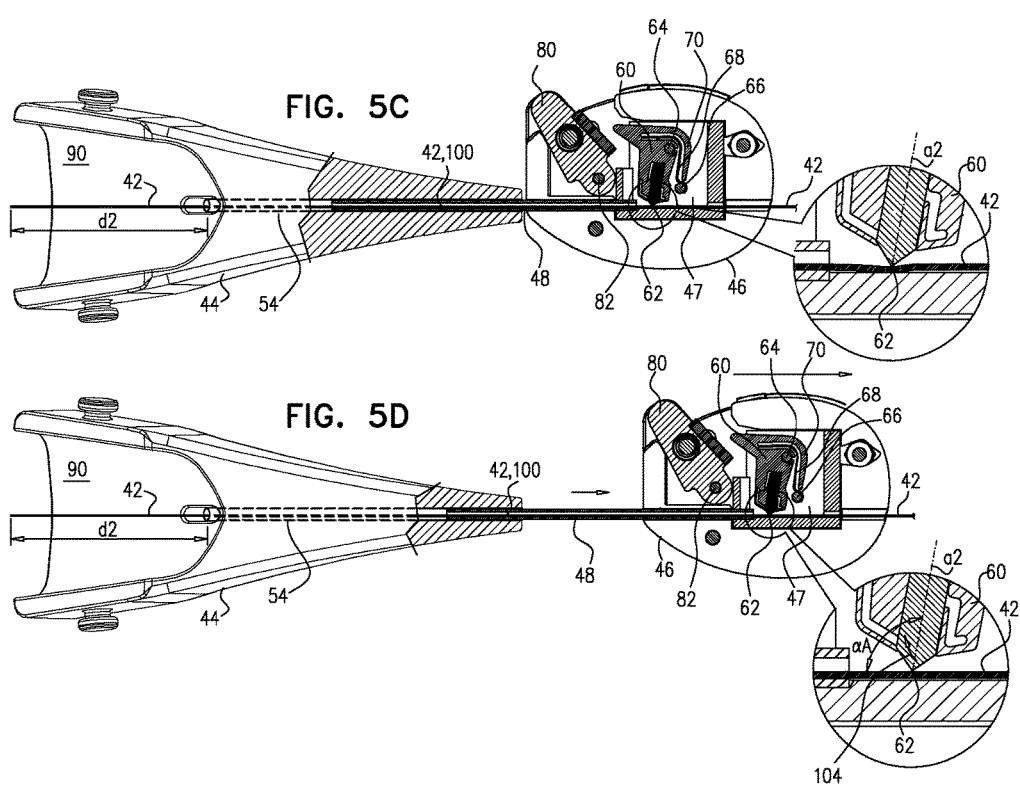

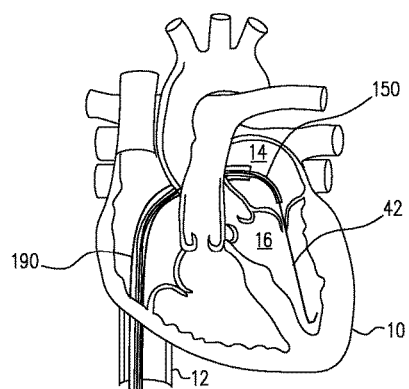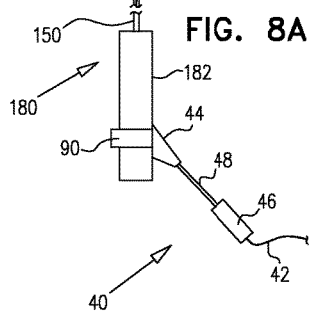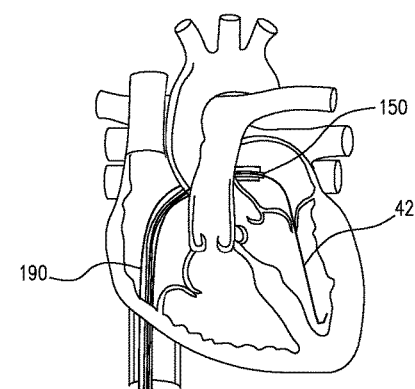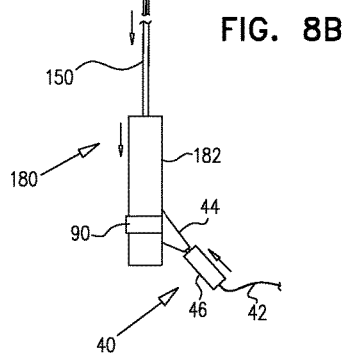
FIG. 8A
FIG. 8B

GUIDEWIRE FEEDER

CROSS-REFERENCES TO RELATED APPLICATIONS

The present application claims priority from U.S. provisional patent application 61/782,121 to Hammer et al., filed Mar. 14, 2013, and entitled "Guidewire Feeder", which is incorporated herein by reference.

FIELD OF THE INVENTION

Some applications of the invention relate to medical apparatus and techniques. Some applications of the invention relate more specifically to apparatus and techniques for percutaneous medical procedures, such as those involving the use of a guidewire.

BACKGROUND

Percutaneous (e.g., transluminal) medical procedures often require the use of a guidewire to facilitate positioning of percutaneous medical devices (e.g., tools, catheters, implants, etc.). Manipulation of the guidewire, such as feeding the guidewire distally into the body of a subject, is often performed by hand.

SUMMARY OF THE INVENTION

A guidewire feeder is provided, comprising a first housing that defines a first channel therethrough, a second housing that defines a second channel therethrough, and a tubular member that is coupled to the second housing and slidably coupled to the first housing. A guidewire disposed within the first channel, the second channel and the tubular member is moved distally through the feeder by repeatedly moving the second housing toward and away from the first housing such that the tubular member slides into and out of the second housing. Each time the second housing is moved toward the first housing, a portion of the guidewire that is disposed within the tubular member is slid distally, with the tubular member, into the first housing. Each time the second housing is moved away from the first housing, the tubular member slides proximally out of the first housing and over the portion of the guidewire, the guidewire remaining stationary with respect to the first housing. Oscillation of the second housing toward and away from the first housing thereby advances the guidewire through the first channel.

A guidewire-engaging element, coupled to the second housing, is configured to facilitate one-way movement of the guidewire through the second channel, and thereby to facilitate the function of the guidewire feeder described hereinabove. For some applications, an engagement switch is configured to move the guidewire-engaging element between an engaged state in which the guidewire feeder functions as described hereinabove, and a disengaged state in which the guidewire is slidable through the second channel in either direction (e.g., so as to facilitate initial threading of the guidewire through the guidewire feeder).

For some applications, the guidewire feeder is configured to be coupled to a medical device for percutaneous procedures. For some applications the guidewire feeder is used to advance the guidewire distally through the medical device. For some applications, the guidewire feeder is used to facilitate withdrawal of the medical device over the guidewire, while maintaining the position of the guidewire (e.g., a distal end thereof) with respect to the body of the subject.

There is therefore provided, in accordance with an application of the present invention, apparatus for use with a guidewire, the apparatus including:

a first housing, shaped to define a first channel through which the guidewire is slidable;

a second housing, shaped to define a second channel through which the guidewire is slidable in at least a first direction toward the first housing;

a guidewire-engaging element, disposed within the second housing, and configured to inhibit the guidewire from sliding through the second channel in a second direction away from the first housing; and a tubular member:
    shaped to define a lumen therethrough, through which the guidewire is slidable, and
    coupled to the second housing and slidably coupled to the first housing.

In an application, the tubular member is slidable within the first channel.

In an application:
the guidewire-engaging element has an engaged state and a disengaged state, and is configured to inhibit the guidewire from sliding through the second channel in the second direction, only when in the engaged state, and
the apparatus further includes an engagement switch, configured to reversibly move the guidewire-engaging element between the engaged state and the disengaged state.

In an application, the apparatus is configured to facilitate percutaneous advancement of the guidewire by a physician, while the physician (a) directly holds the second housing of the device with only one finger and one thumb, and (b) does not directly hold the first housing.

In an application, the lumen of the tubular member provides communication between the first channel and the second channel.

In an application, the tubular member is more rigid than the guidewire, and is configured to inhibit bending of a portion of the guidewire that is disposed within the lumen of the tubular member.

In an application, the first channel, the second channel, and the lumen are collinear.

In an application, the first channel, the second channel, and the lumen define an axis, and the second housing is rotatable around the axis.

In an application, the tubular member is coupled to the second housing and slidably coupled to the first housing such that the second housing is slidable toward the first housing and away from the first housing.

In an application, the apparatus is configured such that, while a portion of the guidewire is disposed within the second channel, when the second housing is moved toward the first housing, the guidewire moves in the first direction.

In an application, the apparatus is configured such that, while the portion of the guidewire is disposed within the second channel, oscillation of the second housing between the first direction and the second direction moves the guidewire in the first direction.

In an application, the apparatus is configured such that, when the second housing slides toward the first housing, the tubular member slides into the first housing.

In an application, the apparatus is configured such that, while the portion of the guidewire is disposed within the second channel, and a portion of the guidewire is disposed within the lumen of the tubular member, when the second housing is moved toward the first housing, the portion of the guidewire that is disposed within the lumen of the tubular member moves while within the tubular member into the first housing, without moving with respect to the tubular member.

In an application, the apparatus is configured such that, when the second housing slides toward the first housing, the tubular member slides into the first channel.

In an application, the apparatus is further for use with a device for facilitating percutaneous procedures, and the first housing is configured to be coupled to the device.

In an application, the first housing includes a coupling member, configured to facilitate coupling the first housing to the device.

In an application, the coupling member includes a generic coupling member, configured to facilitate coupling of the first housing to any of a range of devices for facilitating percutaneous procedures.

In an application, the coupling member includes a strap.

In an application, the guidewire-engaging element is configured such that, while the guidewire is disposed within the second channel, when the guidewire moves in the second direction, the guidewire-engaging element responsively grips the guidewire.

In an application, the guidewire-engaging element is pivotally coupled to the second housing.

In an application, the guidewire-engaging element defines a guidewire-engaging edge, and is configured such that, while the guidewire is disposed within the second channel, the guidewire-engaging edge is disposed against the guidewire at a nonzero angle, such that movement of the guidewire in the second direction through the second channel causes the guidewire-engaging edge to press into the guidewire.

In an application, the guidewire-engaging element is configured such that, while the guidewire is disposed within the second channel, when the guidewire-engaging edge presses into the guidewire, the nonzero angle becomes closer to a right angle.

In an application, the guidewire-engaging element is configured such that, while the guidewire is disposed within the second channel, the guidewire-engaging edge is disposed against the guidewire at a nonzero angle that is not a right angle.

In an application, the guidewire-engaging edge is configured such that, while the guidewire is disposed within the second channel, the guidewire-engaging edge is disposed against the guidewire at an obtuse angle with respect to a portion of the guidewire that is disposed closer to the tubular member than is the guidewire-engaging edge.

There is further provided, in accordance with an application of the present invention, a method for use with a guidewire, the method including:
providing apparatus including:
a first housing,
a second housing, and
a tubular member, coupled to the second housing and slidably coupled to the first housing;
sliding a portion of the guidewire that is disposed within the tubular member in a first direction through the first housing by sliding the tubular member into the first housing by moving the second housing toward the first housing; and
moving the second housing away from the first housing without sliding the guidewire in a second direction through the first housing.

In an application, the method further includes percutaneously advancing the guidewire by sliding the portion of the guidewire in the first direction.

In an application, moving the second housing toward the first housing includes moving the second housing toward the first housing using only one finger and one thumb.

In an application, sliding the tubular member into the first housing includes sliding, into the first housing, a tubular member that is more rigid than the guidewire and is configured to inhibit bending of the portion of the guidewire.

In an application, the method further includes coupling the first housing to a device for facilitating percutaneous procedures.

In an application, the method further includes coupling the first housing to a body of a subject.

In an application, the apparatus includes a guidewire-engaging element, disposed within the second housing, and having an engaged state and a disengaged state, and the method further includes:
feeding the guidewire into at least the second housing while the guidewire-engaging element is in the disengaged state; and
subsequently moving the guidewire-engaging element into the engaged state.

In an application, moving the guidewire-engaging element into the engaged state includes moving the guidewire-engaging element into the engaged state using an engagement switch, configured to reversibly move the guidewire-engaging element between the engaged state and the disengaged state.

In an application, the apparatus includes a guidewire-engaging element coupled to the second housing, and moving the second housing toward the first housing includes moving the second housing toward the first housing such that the guidewire-engaging element responsively grips the guidewire.

In an application, moving the second housing toward the first housing includes moving the second housing toward the first housing such that the guidewire-engaging element responsively pivots with respect to the second housing.

In an application, the guidewire-engaging element defines a guidewire-engaging edge, and moving the second housing toward the first housing includes moving the second housing toward the first housing such that the guidewire-engaging edge presses into the guidewire.

There is further provided, in accordance with an application of the present invention, a method, including:
moving a distal end of a percutaneous medical device in a proximal direction away from an anatomical site of a body of a subject; and
simultaneously, maintaining a position, with respect to the anatomical site, of a distal end of a guidewire that is slidable through the medical device by moving, toward a first housing that is coupled to the medical device, a second housing.

In an application, moving the distal end of the medical device includes pulling a handle of the medical device in the proximal direction using a first hand, and moving the second housing toward the first housing includes moving the second housing toward the first housing using a second hand.

In an application, moving the distal end of the medical device includes moving the distal end of the medical device at a first speed, and moving the second housing toward the first housing includes moving the second housing toward the first housing at a second speed that is relative to the first speed.

In an application, moving the distal end of the medical device includes moving the distal end of the medical device a first distance, and moving the second housing toward the first housing includes moving the second housing toward the first housing a second distance that is relative to the first distance.

In an application, moving the second housing toward the first housing includes moving the second housing toward the first housing such that a guidewire-engaging element, coupled to the second housing, responsively grips the guidewire.

In an application, moving the second housing toward the first housing includes moving the second housing toward the first housing such that the guidewire-engaging element responsively pivots with respect to the second housing.

In an application, the guidewire-engaging element defines a guidewire-engaging edge, and moving the second housing toward the first housing includes moving the second housing toward the first housing such that the guidewire-engaging edge presses into the guidewire.

In an application, the method further includes sliding at least the second housing over a proximal end of the guidewire and distally along the guidewire, and coupling at least the second housing to the medical device.

In an application, sliding at least the second housing distally along the guidewire includes sliding at least the second housing distally along the guidewire while a guidewire-engaging element, coupled to the second housing, is in a disengaged state thereof, and the method further includes, subsequently to coupling at least the second housing to the medical device and prior to maintaining the position of the distal end of the guidewire, moving the guidewire-engaging element into an engaged state thereof.

In an application, moving the guidewire-engaging element into the engaged state includes moving the guidewire-engaging element into the engaged state using an engagement switch, configured to reversibly move the guidewire-engaging element between the engaged state and the disengaged state.

In an application, moving the second housing toward the first housing includes moving the second housing at least 1 cm toward the first housing.

In an application, moving the second housing toward the first housing includes moving the second housing at least 3 cm toward the first housing.

In an application, moving the second housing toward the first housing includes moving the second housing at least 4 cm toward the first housing.

In an application, moving the second housing toward the first housing includes sliding into the first housing, a tubular member that is coupled to the second housing and slidably coupled to the first housing.

In an application, sliding the tubular member into the first housing includes sliding a portion of the guidewire that is disposed within the tubular member into the first housing without the portion of the guidewire moving with respect to the tubular member.

In an application, sliding the tubular member into the first housing includes sliding, into the first housing, a tubular member that is more rigid than the guidewire and is configured to inhibit bending of the portion of the guidewire.

In an application, the method further includes subsequently sliding the tubular member out of the first housing by moving the second housing away from the first housing, without sliding the guidewire with respect to the first housing.

The present invention will be more fully understood from the following detailed description of embodiments thereof, taken together with the drawings, in which:

BRIEF DESCRIPTION OF THE DRAWINGS

FIGS. 3A-B and 4A-B are schematic illustrations of a guidewire feeder, in accordance with some applications of the invention;

FIGS. 5A-D are schematic illustrations of a guidewire feeder being used to advance the guidewire, in accordance with some applications of the invention;

FIGS. 8A-B are schematic illustrations of a guidewire feeder being used to facilitate movement of a medical device with respect to at least a portion of a guidewire, in accordance with some applications of the invention.

DETAILED DESCRIPTION OF EMBODIMENTS

Figure 1:
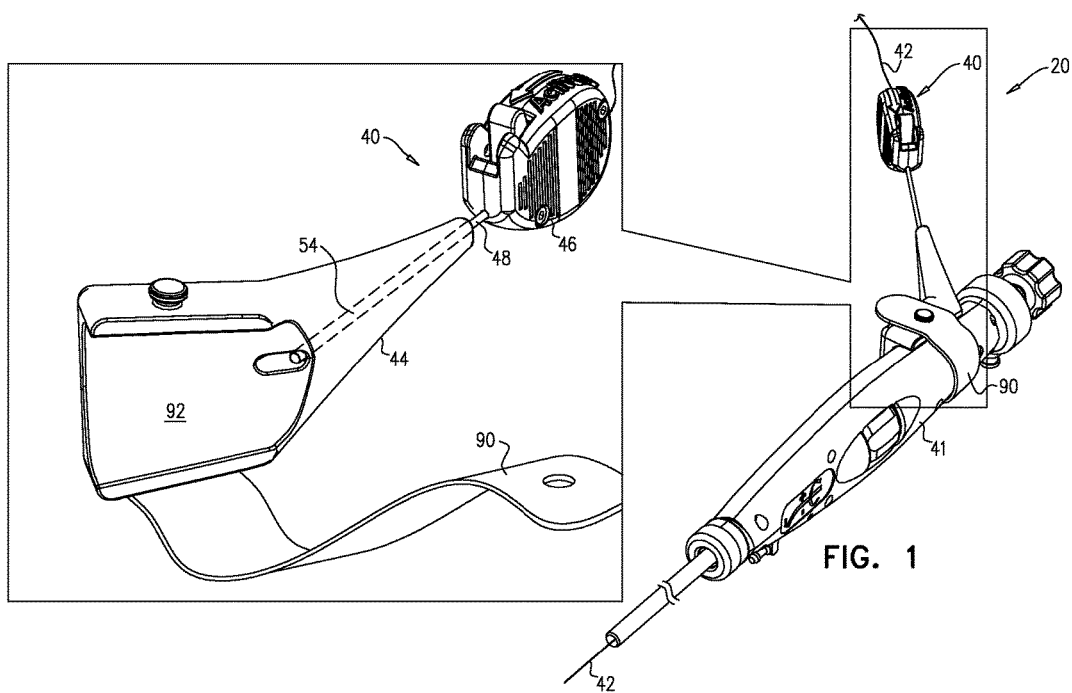
FIGS. 1-2 are schematic illustrations of a guidewire feeder for facilitating handling of a guidewire, in accordance with some applications of the invention.
Figure 2:
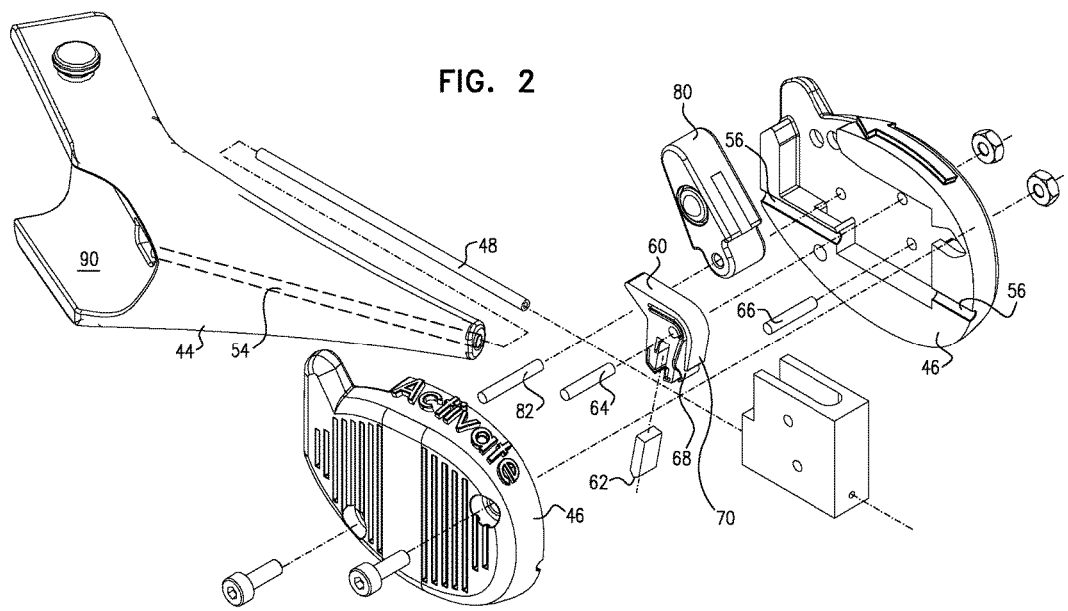

Reference is made to FIGS. 1-2, which are schematic illustrations of a guidewire feeder 40 for facilitating handling of a guidewire 42, in accordance with some applications of the invention. FIG. 1 shows a solid view of guidewire feeder 40 coupled to a medical device 41 for facilitating percutaneous (e.g., transluminal) procedures, and FIG. 2 shows an exploded view of the guidewire feeder. Together, guidewire feeder 40 and guidewire 42 define a system 20. It is to be noted that device 41 is shown as a non-limiting illustrative example of a device to which guidewire feeder 40 is couplable.

Feeder 40 comprises a first housing 44, a second housing 46, and a tubular member 48 that is coupled to the second housing and slidably coupled to the first housing. First housing 44 defines a first channel 54 therethrough, second housing 46 defines a second channel 56 therethrough, and tubular member 48 defines a lumen therethrough. Tubular member 48 (e.g., the lumen thereof) typically provides communication between first channel 54 and second channel 56. First channel 54, tubular member 48, and second channel 56 are typically collinear. Further typically, tubular member 48 is slidably coupled to first housing 44 by being slidable within first channel 54. Tubular member 48 is typically fixedly coupled to second housing, such as by a portion of the tubular member being fixedly coupled within a portion of second channel 56. Feeder 40 further comprises a guidewire-engaging element 60 that is coupled to and/or disposed within second housing 46, and is configured to selectively inhibit the guidewire from sliding through the second channel away from the first housing (e.g., and to not inhibit the guidewire from sliding through the second channel toward the first housing).

Guidewire 42 typically fits snugly within channel 54, channel 56 and/or tubular member 48, but not tightly enough to prevent sliding thereof (e.g., such that the guidewire is subject to friction that is not significantly higher than that to which it is subjected within medical device 41). For some applications, inner surfaces of channel 54, channel 56 and/or tubular member 48 are coated with a low-friction coating so as to further reduce inhibition of advancement of the guidewire. For some applications, guidewire 42 itself is subjected to a friction-reducing treatment (e.g., heat-treated and/or coated with a low-friction coating). Guidewire-engaging element 60 is configured to grip guidewire 42 despite this treatment of the guidewire. Indeed, some prior art guidewires are subjected to a friction-reducing treatment, and feeder 40 may be particularly useful in handling such guidewires.

When second housing 46 is moved toward first housing 44, at least a portion of tubular member 48 slides into the first housing. While a portion of guidewire 42 is disposed within feeder 40, when second housing 46 is moved toward first housing 44, a portion of the guidewire that is disposed within tubular member 48 is pushed, along with the tubular member, into the first housing (e.g., into first channel 54). In contrast, when second housing 46 is moved away from first housing 44, although tubular member 48 slides out of the first housing, the guidewire does not follow. Thereby, oscillation of second housing 46 toward and away from first housing 44 (e.g., along a longitudinal axis a1 defined by first channel 54, tubular member 48, and second channel 56; shown in FIGS. 3B and 4B) moves the guidewire in a single direction through the first housing. This is described in more detail with respect to FIGS. 5A-D.

Percutaneous (e.g., transluminal) guidewires are typically flexible and thereby imparting a pushing force on a guidewire results in bending (e.g., kinking or buckling) of a portion of the guidewire that is distal to the point of pushing, e.g., between the point of pushing and a point of resistance, such as an entry point (e.g., to a body of a subject and/or to another medical device). This makes pushing of the guidewire (e.g., distally into the body of the subject) difficult and/or inefficient. In system 20, the point of pushing is at and/or within second housing 46 (e.g., at guidewire-engaging element 60) and, as shown in FIG. 1, first housing 44 is typically reversibly coupled (e.g., reversibly attached) to the other medical device (e.g., medical device 41), such that guidewire 42 is generally not exposed between the first housing and the medical device. Thereby, guidewire feeder 40 provides rigidity (e.g., support) to the aforementioned portion of the guidewire that is disposed between the pushing point and the entry point to the medical device. Furthermore, for applications in which guidewire 42 extends through the medical device, the guidewire is typically generally not exposed between the first housing and a distal portion of the medical device (i.e., a portion of the medical device that is furthest from feeder 40). Still further, guidewire 42 typically fits snugly within second channel 56, tubular member 48, first channel 54, and the medical device (e.g., a lumen defined by the medical device). Thereby, the guidewire, from the first housing to the distal portion of the medical device, is typically inhibited from bending. It is to be noted that throughout this application, including the specification and the claims, such inhibiting of bending refers to undesired bending (e.g., kinking and/or bucking), such as that described earlier in this paragraph as occurring between a point of pushing and a point of resistance, and does not include desired bending such as that caused by confirmation of the guidewire to a particular shape of feeder and/or medical device 41 (e.g., so as to navigate the vasculature of the subject). Guidewire feeder 40 may alternatively be coupled directly to the body of the subject (e.g., as described hereinbelow with reference to FIG. 6).

It is particularly notable that tubular member 48, which is typically more rigid than guidewire 42, provides rigidity to the portion of the guidewire that is disposed between second housing 46 and first housing 44, and thereby inhibits bending of this portion of the guidewire. The rigidity provided by guidewire feeder 40 (e.g., tubular member 48 thereof) typically allows a longer portion of guidewire 42 to be pushed in each 'stroke', e.g., compared to pushing the guidewire by hand. For example, each oscillation of feeder 40 may advance the guidewire by more than 1 cm, e.g., more than 3 cm, such as more than 4 cm.

It is to be noted that the term "generally not exposed" does not necessarily preclude small portions of the guidewire from being exposed, such as portions that are less than 1 cm in length; typically less than 3 mm of guidewire (e.g., less than 1 mm of guidewire) is exposed. It is also to be noted that although tubular member 48 is typically more rigid than guidewire 42, the tubular member may be somewhat flexible, such as to accommodate use of feeder 40 at different angles, e.g., due to position of the feeder, the subject, the physician, etc.

To facilitate coupling of guidewire feeder 40 to medical device 41 and/or the body of the subject, the guidewire feeder typically comprises a coupling member 90, such as a strap. Coupling member 90 may alternatively or additionally comprise a pin, a latch, and/or another coupling member. Feeder 40 (e.g., first housing 44 thereof) may additionally comprise an indicator, such as a visual and/or tactile indicator to facilitate positioning of the feeder with respect to medical device 41.

For some applications, coupling member 90 is configured to be coupled to a specific medical device, thereby facilitating coupling of feeder 40 to the specific medical device. For some applications, coupling member 90 is couplable to a range of medical devices; that is, the coupling member comprises a generic coupling member. For example, when coupling member 90 comprises a strap, the strap may be placeable around a portion of a medical device without having being matched to that particular medical device. Typically, first housing 44 is shaped to facilitate coupling to the specific medical device and/or the range of medical devices, such as by being shaped to define a concavity 92 in which a portion of the medical device is placeable. Device 41 typically defines a conduit therethrough, and an opening via which the guidewire is introducible into the conduit. Feeder 40 is typically configured to be coupled to device 41 such that first channel 54 (e.g., an end thereof) is aligned with the opening of the conduit of device 41, such that guidewire can slide freely between the second channel and the conduit.

Reference is now made to FIGS. 3A-B, and 4A-B, which are schematic illustrations of guidewire feeder 40, in accordance with some applications of the invention. Typically, guidewire-engaging element 60 is reversibly engageable (e.g., movable between an engaged state and a disengaged state thereof) using an engagement switch 80. FIGS. 3A-B show solid and cross-sectional views, respectively, of feeder 40 in the disengaged state, and FIGS. 4A-B show solid and cross-sectional views, respectively, of the feeder in the engaged state. Typically, guidewire-engaging element 60 is not in contact with guidewire 42 in the disengaged state, and is in contact with the guidewire in the engaged state.

Engagement switch 80 is typically pivotally coupled, by a bearing 82, to second housing 46, such as with at least part of switch 80 being disposed within a space 47 defined by the second housing. An operating physician may move switch 80 (e.g., using a thumb), so as to move element 60 between (1) the disengaged state, in which the guidewire is typically freely slidable in both directions through second channel 56, e.g., so as to introduce the guidewire through the second channel, and (2) the engaged state, in which the guidewire is inhibited from moving through the second channel away from the first housing, e.g., so as to use feeder 40 to advance the guidewire distally into the body of the subject. Typically, engagement switch 80 applies a force to guidewire-engaging element 60 so as to move the guidewire-engaging element into the disengaged state. For example, a spring 68 may be configured to move element 60 into the engaged state by applying a force, and switch 80 may be configured to (1) move the guidewire-engaging element into the disengaged state by applying an opposing force to the force applied by the spring, and (2) move the guidewire-engaging element into the engaged state by removing the opposing force, thereby allowing the spring to move the guidewire-engaging element into the engaged state.

For some applications, guidewire-engaging element 60 defines a protrusion 70 that is configured to abut an abutment (e.g., defined by second housing 46), so as to limit rotation of the guidewire-engaging element around bearing 64, e.g., to prevent guidewire-engaging element from rotating too far when engagement switch 80 moves the guidewire-engaging element into the disengaged state.

Reference is made to FIGS. 5A-D, which are schematic illustrations of guidewire feeder 40, in the engaged state thereof, being used to advance guidewire 42, in accordance with some applications of the invention. While element 60 is in the engaged state, when the guidewire moves through channel 56 toward first housing 44, element 60 responsively grips the guidewire (e.g., increases its grip on the guidewire compared to when the guidewire moves through channel 56 away from the first housing).

For some applications, and as shown in the figures, guidewire-engaging element 60 defines or comprises a guidewire-engaging edge 62 and is configured such that, while the guidewire is disposed within second channel 56, and element 60 is in the engaged state, the guidewire-engaging edge is disposed against the guidewire at an angle such that if the guidewire begins to move through channel 56 away from first housing 44, element 60 grips the guidewire (e.g., edge 62 presses into and/or catches against the guidewire). When guidewire 42 moves through channel 56 toward first housing 44 (i.e., in the opposite direction), guidewire-engaging element 60 does not grip the guidewire, and the guidewire slides past the guidewire-engaging element, typically with edge 62 in light contact with the guidewire. Typically, edge 62 comprises and/or is defined by a hard material, such as cubic zirconia, aluminium oxide (e.g., alpha-aluminium oxide), cemented carbide (e.g., widia), and/or a hardened metal. For some applications, edge 62 defines a plurality of teeth. For some applications, edge 62 comprises a soft material, such as silicone rubber, that applies friction to the guidewire.

Figure 5A:
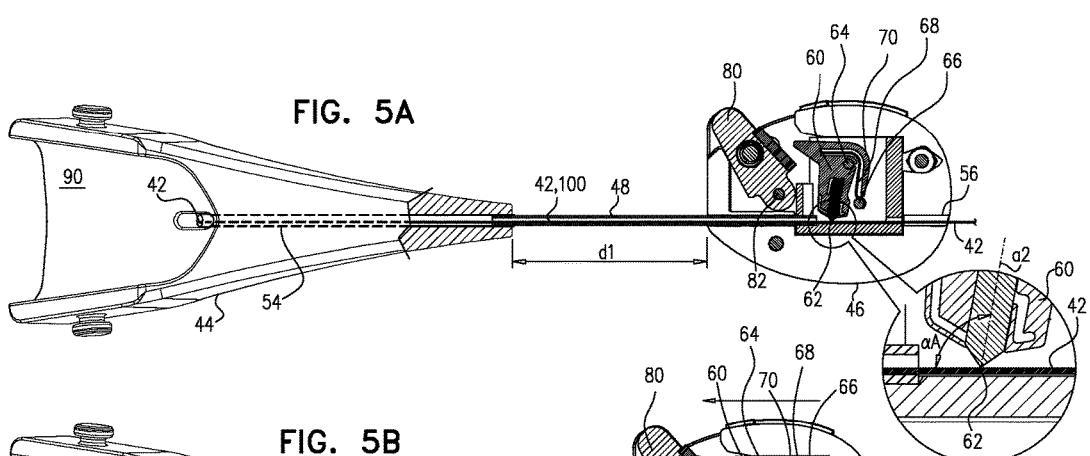

FIG. 5A shows guidewire feeder 40 in a state in which second housing 46 is at a maximum distance d1 from first housing 44 (e.g., a starting position). Typically, when guidewire 42 is stationary within channel 56, guidewire-engaging edge 62 is disposed with respect to guidewire 42 (e.g., against guidewire 42) at a nonzero angle alpha_A that is further typically not a right angle (FIG. 5A). Angle alpha_A is typically an obtuse angle defined between a longitudinal axis a2 of guidewire-engaging edge 62, and a portion of guidewire 42 and/or axis a1 that is disposed closer to tubular member 48 than is the guidewire-engaging edge. An angle defined between guidewire-engaging edge 62 and a portion of channel 56 that is disposed closer to tubular member 48 than is the guidewire-engaging edge, is also typically obtuse.

Guidewire-engaging element 60 is typically pivotally coupled, by a bearing 64, to second housing 46, such as within space 47. Typically, guidewire-engaging element is maintained in the engaged state thereof by spring 68 (e.g., when engagement switch 80 does not hold element 60 in the disengaged state). For example, spring 68 may bias guidewire-engaging element 60 such that edge 62 is disposed against guidewire 42, e.g., by rotating the guidewire-engaging element around bearing 64. That is, spring 68 typically maintains guidewire-engaging element 60 (e.g., guidewire-engaging edge 62 thereof) (1) disposed against guidewire 42, and/or (2) disposed at a predetermined angle with respect to the guidewire.

Figure 5B:
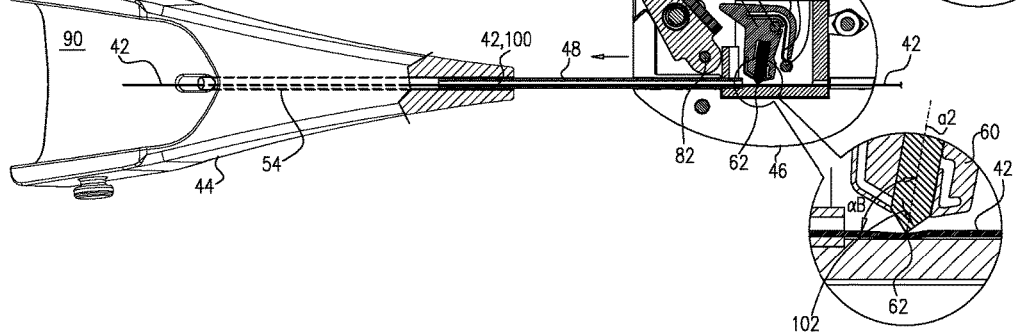

When second housing 46 is moved toward first housing 44, guidewire 42 begins to move through channel 56, guidewire-engaging element 60 responsively grips the guidewire (e.g., edge 62 presses into and/or catches against the guidewire), and the guidewire is thereby pushed toward the first housing (FIG. 5B). Typically, and as shown by arrow 102 in FIG. 5B, guidewire-engaging element 60 grips the guidewire by rotating slightly, e.g., around bearing 64, such that an angle alpha_B, defined between axis a2 and the portion of guidewire 42 and/or axis a1 that is disposed closer to tubular member 48 than is the guidewire-engaging edge, is smaller than angle alpha_A. Angle alpha_B is typically closer to a right angle than is angle alpha_A. It is to be noted that a portion 100 of guidewire 42 that is disposed within tubular member 48 is moved, while stationary within the tubular member, into first channel 54.

FIG. 5C shows second housing 46 stationary at a closest position thereof to first housing 44. Typically, in this position, second housing 46 abuts first housing 44. Although FIG. 5C shows guidewire-engaging element 60 gripping (e.g., edge 62 pressing into and/or catching against) guidewire 42, for some applications, in this stationary position (and/or in other stationary positions), the guidewire-engaging element does not grip the guidewire, but instead only grips the guidewire when the guidewire moves in the appropriate direction with respect to the guidewire-engaging element. It is to be noted that a length d2 of guidewire 42 that has advanced out of first housing 44 since the state shown in FIG. 5A, is typically approximately equal to distance d1.

FIG. 5D shows second housing 46 being moved away from first housing 44 again, e.g., toward the starting position shown in FIG. 5A. When second housing 46 is moved away from first housing 44, guidewire-engaging element 60 does not grip guidewire 42, and the second housing slides over the guidewire, typically with edge 62 in light contact with the guidewire. That is, guidewire 42 moves through channel 56 in the opposite direction to that shown in FIG. 5B. Guidewire 42 typically remains stationary with respect to first housing 44. Typically, and as shown by arrow 104 in FIG. 5D, guidewire-engaging element 60 typically releases its grip on the guidewire by rotating slightly, e.g., around bearing 64, as guidewire 42 begins to move through channel 56. It will be understood that oscillation of second housing 46 toward and away from first housing 44, results in a net movement of guidewire through guidewire feeder 40 in a direction from second housing 46 to first housing 44.

For some applications, some of the force applied to second housing 46 to move the second housing toward first housing 44, increases gripping of guidewire 42 by guidewire-engaging element 60, and release of this force (e.g., when moving the second housing away from the first housing) releases at least some of this gripping (e.g., such that the gripping is overcome by friction between the guidewire and device 41 and/or the first housing).

Figure 6:
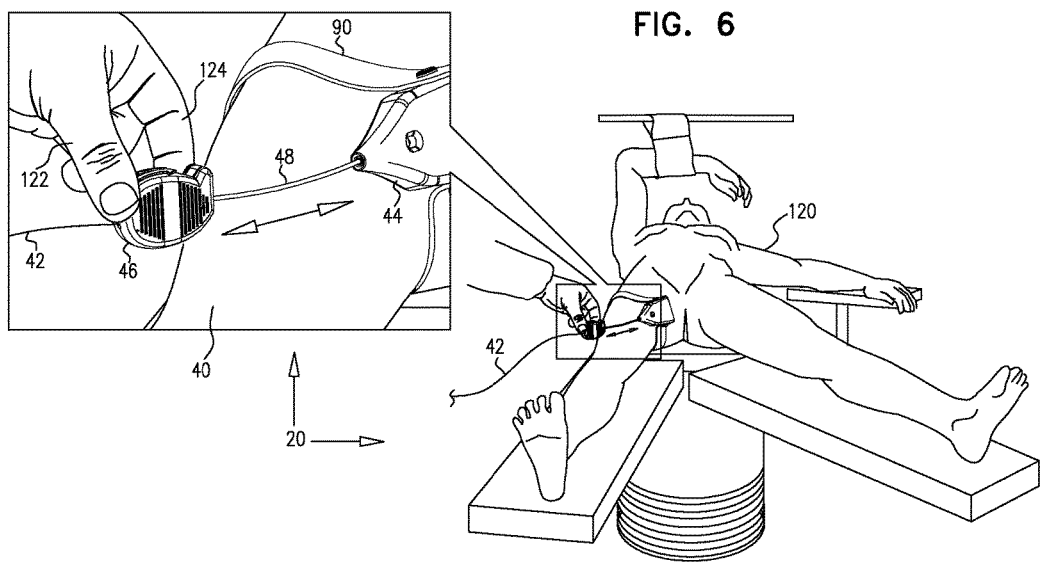
FIG. 6 is a schematic illustration of a guidewire feeder being used to advance the guidewire into the femoral vein of a subject, in accordance with some applications of the invention.

Reference is made to FIG. 6, which is a schematic illustration of guidewire feeder 40 being used to advance guidewire 42 into the femoral vein of a subject 120, in accordance with some applications of the invention. As described hereinabove (e.g., with reference to FIG. 1), for some applications guidewire feeder 40 is configured to be used with another medical device, typically by being coupled to the other medical device (e.g., using coupling member 90). For some applications, and as shown in FIG. 6, guidewire feeder 40 is configured to be coupled to the subject being treated, such as by securing coupling member 90 around the thigh of the subject. For some such applications, first housing 44 is shaped to define, or is coupled to, a cannula that facilitates entry of guidewire 42 into a blood vessel of the subject, such as the femoral vein of the subject (e.g., as described with reference to FIG. 7, mutatis mutandis). It is to be noted that guidewire feeder 140, described with reference to FIG. 7, may be used with the techniques described with reference to FIG. 6, mutatis mutandis.

Figure 7:
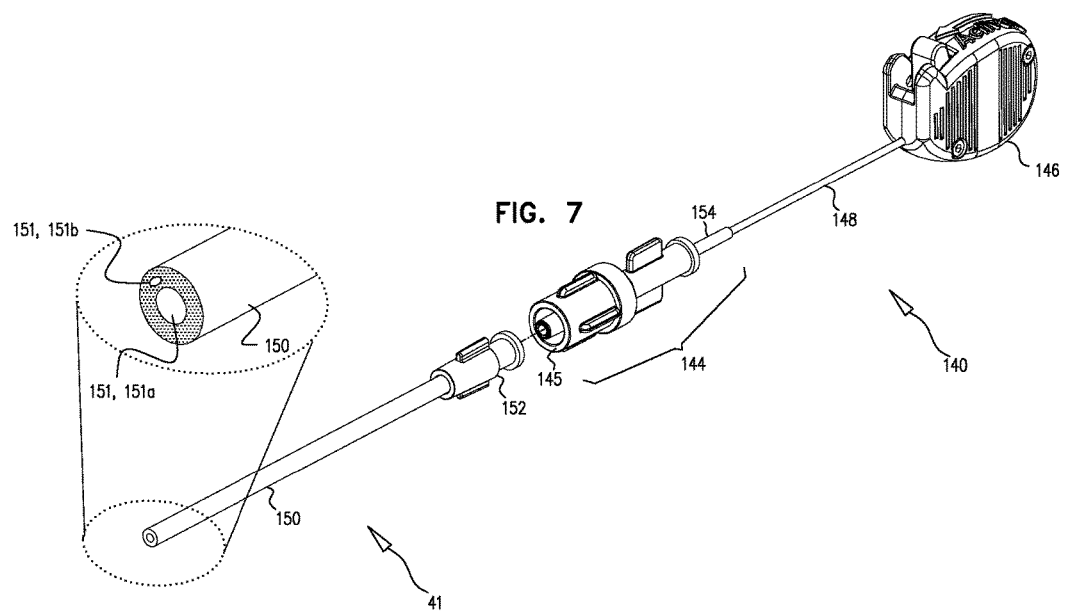
FIG. 7 is a schematic illustration of a guidewire feeder, for use with the guidewire and a cannula, in accordance with some applications of the invention.

Reference is made to FIG. 7, which is a schematic illustration of a guidewire feeder 140, for use with guidewire 42 and a cannula 150 that defines at least a first lumen 151 therethrough, in accordance with some applications of the invention. Together, guidewire feeder 140 and cannula 150 define a system 160. System 160 typically further comprises guidewire 42, described hereinabove. For some applications, cannula 150 defines a secondary lumen 153 in the wall of the catheter, lumen 153 typically providing dedicated access for guidewire 42, and lumen 151 typically providing access for other apparatus. Typically, when a dedicated guidewire lumen such as lumen 153 is provided, the guidewire fits snugly within that lumen. It is hypothesized that this snug fit facilitates the pushing of the guidewire without the guidewire bending, and/or makes the use of guidewire feeder 40 more advantageous due to increased friction on the guidewire.

For some applications guidewire feeder 140 comprises the same components of and/or performs the same functions of guidewire feeder 40, described hereinabove, mutatis mutandis. For example, guidewire feeder 140 comprises a first housing 144, a second housing 146, and a tubular member 148 that is coupled to the second housing and slidably coupled to the first housing. First housing 144 defines or is coupled to a pipe 154 that defines a first channel therethrough, which is typically analogous to first channel 54 of guidewire feeder 40, described hereinabove. Second housing 146 defines a second channel therethrough (not shown), and tubular member 148 defines a lumen therethrough, and provides communication between the first channel and the second channel. Typically, tubular member 148 is slidably coupled to first housing 144 by being slidable within pipe 154 (e.g., within the first channel). Tubular member 148 is typically fixedly coupled to second housing, such as by a portion of the tubular member being fixedly coupled within a portion of the second channel. Guidewire feeder 140 further comprises a guidewire-engaging element (not shown) that is coupled to and/or disposed within second housing 146, and is configured to selectively inhibit the guidewire from sliding through the second channel away from the first housing.

Typically, the guidewire-engaging element of guidewire feeder 140 comprises guidewire-engaging element 60, described hereinabove. As described hereinabove for guidewire feeder 40, oscillation of the second housing toward and away from the first housing moves the guidewire disposed therewithin in a single direction through the first housing. First housing 144 is configured to be reversibly coupled (e.g., reversibly attached) to cannula 150, so as to facilitate advancement of guidewire 42 into the body of the subject, e.g., as described for the coupling of guidewire feeder 40 to medical device 41 hereinabove, mutatis mutandis. For some applications, cannula 150 comprises medical device 41. Cannula 150 typically comprises a coupling portion 152, configured to be reversibly coupled to first housing 144, which is typically shaped to define a complementary coupling portion 145. For some applications, coupling portion 152 comprises a valve or similar element to inhibit blood from flowing out via the coupling portion. For some applications, coupling portions 152 and 145 comprise Luer-type fittings. For some applications, guidewire-feeder 140 is configured to be coupled to a generic cannula (e.g., cannula 150 defines a generic cannula). For some applications, guidewire feeder 140 is identical to guidewire feeder 40, except for the shape and/or coupling properties of first housing 144. It is to be noted that in this context, throughout this application, including the specification and the claims, the term "cannula" is used as a general term for a percutaneous access device, and may include, by way of example and not limitation, a hollow needle or a catheter.

Typically, guidewire 42 is typically generally not exposed between second housing 146 and a distal end of cannula 150 (i.e., the end of the cannula that is furthest from feeder 140). For example, cannula 150 may be transluminally advanced to the heart of the subject, and guidewire 42 is enclosed within feeder 140 and cannula 150, from when the guidewire enters second housing 146 until it emerges from the distal end of the cannula in the heart of the subject. That is, the guidewire is inhibited from bending from a point of pushing of the guidewire (i.e., second housing 146, e.g., the guidewire-engaging element thereof), to the distal end of the cannula.

Reference is made to FIGS. 8A-B, which are schematic illustrations of guidewire feeder 40 being used to facilitate movement of a medical device 180 with respect to at least a portion of guidewire 42, in accordance with some applications of the invention. For some applications, medical device 180 comprises medical device 41, described hereinabove. For some applications, medical device 180 comprises a handle 182 and a cannula, such as cannula 150, described with reference to FIG. 7, mutatis mutandis. Guidewire feeder 40 is couplable to device 180 such that first housing 44 (e.g., first channel 54 thereof) is aligned with an entry point on device 180 for guidewire 42. Typically, guidewire feeder 40 is couplable to handle 182 using coupling member 90, handle 182 defining the entry point for guidewire 42 into device 180.

FIG. 8A shows medical device 180 with cannula 150 thereof having been advanced into the subject (e.g., percutaneously advanced, such as transluminally advanced). By way of illustration and not limitation, cannula 150 is shown having been advanced transfemorally, via inferior vena cava 12 of the subject, transseptally into left atrium 14 of the heart, and into left ventricle 16 of the heart. For some applications, and as shown in FIGS. 8A-B, cannula 150 is advanced via an outer sheath 190. FIG. 8A shows guidewire 42 disposed within cannula 150. For example, cannula 150 may have been advanced to the heart over guidewire 42. Alternatively, guidewire 42 may have been advanced through cannula 150 (e.g., using feeder 40) subsequent to the advancement of the cannula. For some applications, it is desirable to subsequently move guidewire 42 with respect to device 180 (e.g., cannula 150 thereof).

Moving guidewire 42 proximally with respect to device 180 is typically not challenging. For example, to withdraw guidewire 42 from the body of the subject, a pulling force is typically applied to the guidewire to pull the guidewire proximally while holding device 180 still. Similarly, to initially advance device 180 over guidewire 42, device 180 is pushed distally while maintaining a pulling force to the guidewire to hold the guidewire still. In contrast, and as described hereinabove, moving guidewire 42 distally with respect to device 180 (e.g., by applying a pushing force to the guidewire) is typically difficult and/or inefficient due to bending of the portion of the guidewire that is between the point of pushing and a point of entry of the guidewire into device 180. Guidewire feeder 40 may be used to initially advance (e.g., push) guidewire 42 through medical device 180, such as in a manner described hereinabove, mutatis mutandis. Furthermore, and as shown in FIGS. 8A-B, feeder 40 may be used to facilitate withdrawal of device 180 from the body of the subject, while keeping guidewire 42 still with respect to the body of the subject, e.g., so as to facilitate the subsequent advancement of another medical device and/or an implant over the same guidewire.

As described hereinabove, FIG. 8A shows cannula 150 of medical device 180 having been advanced into the subject, and guidewire 42 disposed within the cannula. An operating physician withdraws cannula 150 proximally (e.g., by pulling handle 182 proximally) while simultaneously pushing second housing 46 of feeder 40 toward first housing 44, thereby applying a pushing force on guidewire 42, such that the distal end of the guidewire remains stationary with respect to the body of the subject (FIG. 8B). Typically, the distance and/or speed that second housing 46 is pushed toward first housing 44 is relative (although not necessarily identical) to the distance and/or speed that the cannula is withdrawn. Second housing 46 is subsequently moved away from first housing 44, and the process is repeated (e.g., the second housing is oscillated) until a desired degree of withdrawal of cannula 150 (e.g., complete withdrawal from the body of the subject) is achieved. Typically, the operating physician holds medical device 180 (e.g., handle 182 thereof) with one hand, and operates feeder 40 with the other hand (e.g., by holding second housing 46 with the thumb and forefinger).

Guidewire feeder 40 is particularly advantageous in transluminal (e.g., transfemoral) cardiac procedures, for which withdrawal of cannula 150 typically comprises withdrawal over greater than 80 cm (e.g., greater than 1 m), e.g., due to the increased 'stroke' length described hereinabove. For some applications, imaging (e.g., fluoroscopy and/or echo) are used to observe the position of cannula 150 and/or guidewire 42 within the body of the subject, such as in real-time so as to facilitate maintenance of the position of the distal end of the guidewire, while retracting cannula 150 from the subject.

Reference is again made to FIGS. 7 and 8A-B. It is to be noted that guidewire feeder 140, described with reference to FIG. 7, may also be used with the techniques described with reference to FIGS. 8A-B.

Reference is again made to FIGS. 1-8. Typically, second housing 46 is shaped to define a handle that is configured (e.g., shaped) to facilitate gripping and operation thereof by the operating physician using only a thumb 122 and forefinger 124 (e.g., as shown in FIG. 6). For some applications, such gripping of second housing 46 by the operating physician is the only point at which the operating physician directly contacts guidewire feeder 40.

Reference is again made to FIGS. 1-8. Although first housing 44 and second housing 46 are shown throughout in the same rotational position around axis a1 with respect to each other, the housings are typically rotatable around axis a1 with respect to each other. For example, while first housing is coupled to medical device 41, second housing 46 is typically freely rotatable around axis a1. For some applications, such free rotation is facilitated by tubular member 48 being freely rotatable within first channel 56. Such free rotation may facilitate effective and/or comfortable use of guidewire feeder 40 by the operating physician. For some applications, this free rotation is partly inhibited while second housing 46 is being pushed toward first housing 44, and guidewire-engaging element 60 is gripping guidewire 42 (e.g., due to the gripping of the guidewire by the guidewire-engaging element).

Reference is again made to FIGS. 1-8. It is to be noted that, although the example of a guidewire (i.e., guidewire 42) is used throughout this application, feeder 40 may also be used to facilitate feeding of other longitudinal (and typically flexible) elements, such as tubular longitudinal elements, e.g., catheters, mutatis mutandis.

Reference is again made to FIGS. 1-8. For some applications, guidewire feeder 40 is integrated with a medical device, such as device 41 or device 180. For example, handle 182 of device 180 may define the first housing of the guidewire feeder, tubular member 48 being slidably coupled to the handle.

It will be understood that, although the terms "first," "second," etc. may be used in the present application (including the specification and the claims) to describe various elements and/or directions, these terms should not be limiting. These terms are only used to distinguish one element and/or direction from another. Thus, a "first" element described herein could also be termed a "second" element without departing from the teachings of the present disclosure.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a guidewire, the apparatus comprising a guidewire feeder, which comprises:
   a first housing, shaped to define a first channel through which the guidewire is slidable;
   a second housing, shaped to define a second channel through which the guidewire is slidable in at least a first direction toward the first housing;
   a guidewire-engaging element, which is disposed within the second housing, and which is configured to inhibit the guidewire from sliding through the second channel in a second direction away from the first housing, and to allow the guidewire to slide through the second channel in the first direction toward the first housing; and
   a tubular member, which is shaped to define a lumen through which the guidewire is slidable, is coupled to the second housings and is slidably coupled to the first housing, such that the second housing is slidable in directions toward and away from the first housing,
   wherein the guidewire feeder is arranged such that oscillation of the second housing toward and away from the first housing advances the guidewire in the first direction through the first channel of the first housing, by:
      movement of the second housing toward the first housing sliding a portion of the guidewire that is disposed within the tubular member in the first direction, with the tubular member, into the first housing, and movement of the second housing away from the first housing sliding the tubular member in the second direction out of the first housing and over the portion of the guidewire, while the guidewire remains stationary with respect to the first housing.

2. The apparatus according to claim 1, wherein the tubular member is slidable within the first channel.

3. The apparatus according to claim 1, wherein:
the guidewire-engaging element has an engaged state and a disengaged state, and is configured to inhibit the guidewire from sliding through the second channel in the second direction, only when in the engaged state, and
the apparatus further comprises an engagement switch, configured to reversibly move the guidewire-engaging element between the engaged state and the disengaged state.

4. The apparatus according to claim 1, wherein the apparatus is configured to facilitate percutaneous advancement of the guidewire by a physician, while the physician (a) directly holds the second housing of the apparatus with only one finger and one thumb, and (b) does not directly hold the first housing.

5. The apparatus according to claim 1, wherein the lumen of the tubular member provides communication between the first channel and the second channel.

6. The apparatus according to claim 1, further comprising the guidewire, wherein the tubular member is more rigid than the guidewire, and
is configured to inhibit bending of the portion of the guidewire that is disposed within the lumen of the tubular member.

7. The apparatus according to claim 1, wherein the first channel, the second channel, and the lumen are collinear.

8. The apparatus according to claim 7, wherein the first channel, the second channel, and the lumen define an axis, and wherein the second housing is rotatable around the axis.

9. The apparatus according to claim 2, wherein the apparatus is configured such that, when the second housing slides toward the first housing, the tubular member slides into the first channel.

10. The apparatus according to claim 1, wherein the apparatus is further for use with a device for facilitating percutaneous procedures, and wherein the first housing is configured to be coupled to the device.

11. The apparatus according to claim 10, wherein the first housing comprises coupling means, configured to facilitate coupling the first housing to the device.

12. The apparatus according to claim 1, wherein the guidewire-engaging element is configured to inhibit the guidewire from sliding through the second channel in the second direction by gripping the guidewire.

13. The apparatus according to claim 12, wherein the guidewire-engaging element is pivotally coupled to the second housing.

14. The apparatus according to claim 12, wherein the guidewire-engaging element defines a guidewire-engaging edge, and is configured such that, while the guidewire is disposed within the second channel, the guidewire-engaging edge is disposed against the guidewire at an angle, such that movement of the guidewire in the second direction through the second channel causes the guidewire-engaging edge to press into the guidewire.

15. The apparatus according to claim 14,
wherein the angle is with respect to a portion of the guidewire that is disposed closer to the tubular member than is the guidewire-engaging edge, and
wherein the guidewire-engaging element is configured such that, while the guidewire is disposed within the second channel:
when the second housing is moved toward the first housing, the guidewire-engaging edge pushes the guidewire toward the first housing by pressing into the guidewire by rotating such that the angle decreases and becomes closer to a right angle.

16. The apparatus according to claim 14, wherein the guidewire-engaging edge is configured such that, while the guidewire is disposed within the second channel, the guidewire-engaging edge is disposed against the guidewire at an obtuse angle with respect to a portion of the guidewire that is disposed closer to the tubular member than is the guidewire-engaging edge.

17. A method for use with a guidewire, the method comprising:
providing a guidewire feeder including:
a first housing, shaped to define a first channel through which the guidewire is slidable;
a second housing, shaped to define a second channel through which the guidewire is slidable in at least a first direction toward the first housing;
a guidewire-engaging element, which is disposed within the second housing, and which is configured to inhibit the guidewire from sliding through the second channel in a second direction away from the first housing, and to allow the guidewire to slide through the second channel in the first direction toward the first housing; and
a tubular member, which is shaped to define a lumen through which the guidewire is slidable, is coupled to the second housing, and is slidably coupled to the first housing, such that the second housing is slidable in directions toward and away from the first housing; and
advancing the guidewire in the first direction through the first channel of the first housing by oscillating the second housing toward and away from the first housing by:
sliding a portion of the guidewire that is disposed within the tubular member in the first direction through the first housing by sliding the tubular member into the first housing, by moving the second housing toward the first housing; and
sliding the tubular member in the second direction out of the first housing and over the portion of the guidewire by moving the second housing away from the first housing, while the guidewire remains stationary with respect to the first housing.

18. The method according to claim 17, wherein providing the guidewire feeder comprises providing the guidewire feeder in which the guidewire-engaging element is configured to inhibit the guidewire from sliding through the second channel in the second direction by gripping the guidewire.

19. The method according to claim 17, wherein the tubular member is slidable within the first channel.

20. The method according to claim 19, wherein the apparatus is configured such that, when the second housing slides toward the first housing, the tubular member slides into the first channel.

* * * * *